(12) United States Patent
Scharschmidt et al.

(10) Patent No.: US 10,045,959 B1
(45) Date of Patent: *Aug. 14, 2018

(54) METHODS OF THERAPEUTIC MONITORING OF NITROGEN SCAVENGING DRUGS

(71) Applicant: Horizon Therapeutics, LLC, Lake Forest, IL (US)

(72) Inventors: Bruce Scharschmidt, San Francisco, CA (US); Masoud Mokhtarani, Walnut Creek, CA (US)

(73) Assignee: Horizon Therapeutics, LLC, Lake Forest, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/944,416

(22) Filed: Apr. 3, 2018

Related U.S. Application Data

(60) Continuation of application No. 15/687,132, filed on Aug. 25, 2017, now Pat. No. 9,962,359, which is a
(Continued)

(51) Int. Cl.
*A61K 31/216* (2006.01)
*A61K 9/00* (2006.01)
(Continued)

(52) U.S. Cl.
CPC .......... *A61K 31/235* (2013.01); *A61K 9/0053* (2013.01); *A61K 31/216* (2013.01); *G01N 31/221* (2013.01); *G01N 33/4925* (2013.01); *G01N 33/84* (2013.01); *G01N 2800/04* (2013.01); *G01N 2800/085* (2013.01); *G01N 2800/52* (2013.01); *Y10T 436/175383* (2015.01)

(58) Field of Classification Search
CPC .. A61K 31/216; A61K 31/235; A61K 9/0053; G01N 2800/04; G01N 2800/085; G01N 2800/52; G01N 31/221; G01N 33/4925; G01N 33/84; Y10T 436/175383
See application file for complete search history.

(56) References Cited

U.S. PATENT DOCUMENTS 3,686,238 A    8/1972  Zaffaroni
4,284,647 A    8/1981  Brusilow
(Continued)

FOREIGN PATENT DOCUMENTS

CN    1778963         5/2006
CN    103304402 A     9/2013
(Continued)

OTHER PUBLICATIONS

"Program for SIMD annual meeting", Molecular Genetics and Metabolism, (Mar. 1, 2012), vol. 105, No. 3, doi:10.1016/j.ymgme.2012.01.004, ISSN 1096-7192, pp. 273-366, XP055202401.
(Continued)

*Primary Examiner* — Savitha M Rao
(74) *Attorney, Agent, or Firm* — Chris Marion

(57) ABSTRACT

The present disclosure provides methods for evaluating daily ammonia exposure based on a single fasting ammonia blood level measurement, as well as methods that utilize this technique to adjust the dosage of a nitrogen scavenging drug, determine whether to administer a nitrogen scavenging drug, and treat nitrogen retention disorders.

9 Claims, 4 Drawing Sheets

Related U.S. Application Data continuation of application No. 15/457,643, filed on Mar. 13, 2017, which is a continuation of application No. 15/074,691, filed on Mar. 18, 2016, now abandoned, which is a continuation of application No. 14/958,259, filed on Dec. 3, 2015, now Pat. No. 9,326,966, which is a continuation of application No. 14/816,674, filed on Aug. 3, 2015, now Pat. No. 9,254,278, which is a continuation of application No. 13/775,000, filed on Feb. 22, 2013, now Pat. No. 9,095,559, which is a division of application No. 13/417,137, filed on Mar. 9, 2012, now Pat. No. 8,404,215.

(60) Provisional application No. 61/564,668, filed on Nov. 29, 2011, provisional application No. 61/542,100, filed on Sep. 30, 2011.

(51) Int. Cl.
  *G01N 33/49* (2006.01)
  *A61K 31/235* (2006.01)
  *G01N 31/22* (2006.01)
  *G01N 33/84* (2006.01)

(56) References Cited

U.S. PATENT DOCUMENTS

| | | | |
|---|---|---|---|
| 4,457,942 | A | 7/1984 | Brusilow |
| 5,654,333 | A | 8/1997 | Samid |
| 5,968,979 | A | 10/1999 | Brusilow |
| 6,060,510 | A | 5/2000 | Brusilow |
| 6,083,984 | A | 7/2000 | Brusilow |
| 6,219,567 | B1 | 4/2001 | Eggers |
| 6,825,384 | B1 | 11/2004 | Prakash |
| 8,094,521 | B2 | 1/2012 | Levy |
| 8,404,215 | B1 | 3/2013 | Scharschmidt |
| 8,642,012 | B2 | 2/2014 | Scharschmidt |
| 9,078,865 | B2 | 7/2015 | Lee |
| 9,095,559 | B2 | 8/2015 | Scharschmidt |
| 9,254,278 | B2 | 2/2016 | Scharschmidt |
| 9,289,406 | B2 | 3/2016 | Scharschmidt |
| 9,326,966 | B2 | 5/2016 | Scharschmidt |
| 2003/0195255 | A1 | 10/2003 | Summar |
| 2004/0229948 | A1 | 11/2004 | Summar |
| 2005/0273359 | A1 | 12/2005 | Young |
| 2006/0135612 | A1 | 6/2006 | Ferrante |
| 2008/0119554 | A1 | 5/2008 | Jalan |
| 2010/0008859 | A1 | 1/2010 | Scharschmidt |
| 2010/0016207 | A1 | 1/2010 | Wurtman |
| 2012/0022157 | A1 | 1/2012 | Scharschmidt |
| 2012/0220661 | A1 | 8/2012 | Lee |
| 2013/0085179 | A1 | 4/2013 | Scharschmidt |
| 2013/0172543 | A1 | 7/2013 | Iwabuchi |
| 2013/0210914 | A1 | 8/2013 | Scharschmidt |
| 2013/0281530 | A1 | 10/2013 | Scharschmidt |
| 2014/0142186 | A1 | 5/2014 | Scharschmidt |
| 2015/0094278 | A1 | 4/2015 | Scharschmidt |
| 2015/0105469 | A1 | 4/2015 | Scharschmidt |
| 2015/0335605 | A1 | 11/2015 | Scharschmidt |
| 2016/0074356 | A1 | 3/2016 | Scharschmidt |
| 2016/0081969 | A1 | 3/2016 | Scharschmidt |
| 2016/0199332 | A1 | 7/2016 | Scharschmidt |
| 2016/0199333 | A1 | 7/2016 | Scharschmidt |
| 2016/0199334 | A1 | 7/2016 | Scharschmidt |
| 2016/0202240 | A1 | 7/2016 | Scharschmidt |
| 2016/0223520 | A1 | 8/2016 | Scharschmidt |
| 2017/0354631 | A1 | 12/2017 | Scharschmidt |
| 2017/0354632 | A1 | 12/2017 | Scharschmidt |
| 2018/0015064 | A1 | 1/2018 | Scharschmidt |
| 2018/0015065 | A1 | 1/2018 | Scharschmidt |
| 2018/0021291 | A1 | 1/2018 | Scharschmidt |
| 2018/0021292 | A1 | 1/2018 | Scharschmidt |
| 2018/0021293 | A1 | 1/2018 | Scharschmidt |

FOREIGN PATENT DOCUMENTS

| | | |
|---|---|---|
| EP | 2607366 A1 | 6/2013 |
| IT | 1317073 B1 | 5/2003 |
| WO | 199422494 | 10/1994 |
| WO | 2005053607 A2 | 6/2005 |
| WO | 2005053607 A3 | 6/2005 |
| WO | 2006056794 A1 | 6/2006 |
| WO | 2007005633 A2 | 1/2007 |
| WO | 2009087474 A2 | 7/2009 |
| WO | 2009087474 A3 | 7/2009 |
| WO | 2009134460 A1 | 11/2009 |
| WO | 2009145323 | 12/2009 |
| WO | 2010025303 A1 | 3/2010 |
| WO | 2011011781 A1 | 1/2011 |
| WO | 2012028620 A1 | 3/2012 |
| WO | 2013048558 A2 | 4/2013 |
| WO | 2013158145 A1 | 10/2013 |
| WO | 2015063659 | 5/2015 |

OTHER PUBLICATIONS

Ahrens, M. et al. (Jan. 2001). 'Consensus Statement From a Conference for the Management of Patients With Urea Cycle Disorders.' Supp. Journal of Pediatrics 138(1):S1-S5.

Ambrose, A.M. et al. (1933). 'Further Studies on the Detoxification of Phenylacetic Acid,' J. Bio. Chem. 101:669-675.

Amended Complaint, *Horizon Therapeutics, Inc. v. Lupin Ltd. and Lupin Pharmaceuticals Inc.* Filed in U.S. District Court for the District of New Jersey, Apr. 6, 2016, 10 pgs.

Amodio, P., et al., "Detection of Minimal Hepatic Encephalopathy: Normalization and Optimization of the Psychometric Hepatic Encephalopathy Score. A Neuropsychological and Quantified EEG Study," J. Hepatol. 49:346-353 (2008).

ANDA Notice Letter, Lupin Ltd. to Horizon Therapeutics, Inc.. Re: NOtitication of invalidity, Unenforceability, and/or Noninfringement for U.S. Pat. No. 8,404,215 and U.S. Pat. No. 8,642,012 Pursuant to 505(j)(2)(B)(ii) and (iv) of the Federal Food, Drug, and Cosmetic Act, Sep. 4, 2015.

ANDA Notice Letter, Lupin Ltd. to Horizon Therapeutics, Inc.. Re: Notification of Invalidity, Unenforceability, and/or Noninfringement for U.S. Pat. No. 9,095,559 Pursuant to 505(j)(2)(B)(ii) and (iv) of the Federal Food, Drug, and Cosmetic Act, Nov. 6, 2015, 30 pgs.

ANDA Notice Letter, Lupin Ltd. to Horizon Therapeutics, Inc.. Re: Notification of Invalidity, Unenforceability, and/or Noninfringement for U.S. Pat. No. 9,254,278 Pursuant to 505(j)(2)(B)(ii) and (iv) of the Federal Food, Drug, and Cosmetic Act, Apr. 13, 2016, 42 pgs.

ANDA Notice Letter, Par Pharmaceutical, Inc. to Hyperion Therapeutics, inc.. Re: Glycerol Phenylbutyrate 1.1 gm/ml oral liquid; U.S. Pat. No. 8,404,215 and U.S. Pat. No. 8,642,012 Notice of Paragraph IV Certification Mar. 12, 2014, 27 pgs.

Anonymous, "Application No. 20-645 Medical Review FDA", (Feb. 15, 2005), pp. 1-55, URL: http://www.accessdata.fda.gov/drugsatfda_docs/nda/2005/020645s000_MedR.pdf, (Mar. 22, 2016), XP055260195.

Bajaj, J. S., et al., 'Review Article: The Design of Clinical Trials in Hepatic Encephalopathy—An International Society for Hepatic Encephalopathy and Nitrogen Metabolism (ISHEN) Consensus Statement,' Aliment Pharmacol Ther. 33 (7):739-747 (2011).

Barsotti, 'Measurement of Ammonia in Blood', 138 J. Pediatrics, S11-S20 (2001).

Batshaw M.L. et al. (Jun. 10, 1982) 'Treatment of Inborn Errors of Urea Synthesis: Activation of Alternative Pathways of Waste Nitrogen Synthesis and Excretion,' N Engl J Med 306(23):1387-1392.

Batshaw, M. L. et. al., Alternative Pathway Therapy for Urea Cycle Disorder: Twenty Years Later, 138 J. Pediatrics S46 (2001).

Batshaw, M.L. (1984). 'Hyperammonemia,' in Current Problems in Pediatrics, Lockhart, J.D. ed.: Year Book Medical Publishers, pp. 2-69.

Batshaw, M.L. et al. (Aug. 1981) 'New Approaches to the Diagnosis and Treatment of Inborn Errors of Urea Synthesis,' Pediatrics 68(2):290-297.

(56) References Cited

OTHER PUBLICATIONS

Batshaw, M.L. et al. (Dec. 1980). 'Treatment of Hyperammonemic Coma Caused by Inborn Errors of Urea Synthesis,' J. Pediatr. 97(6):893-900.
Batshaw, M.L. et al., Treatment of Carbamyl Phosphate Synthetase Deficiency with Keto Analogues of Essential Amino Acids, 292 The New England J. Medicine, 1085-1090 (1975).
Berry, G. T., et al., 'Long-Term Management of Patients with Urea Cycle Disorders,' J. Pediatrics (2001) 138:S56-S61.
Blau, Duran, Blaskovics, Gibson (editors), Physcian's Guide to the Laboratory Diagnosis of Metabolic Diseases, 261-276 (2d ed. 1996).
Blei, A. T., et al., 'Hepatic Encephalopathy,' Am. J. Gastroenterol. 96(7): 1968-1976 (2001).
Brahe, C., et al., (2005) 'Phenylbutyrate Increases SMN Gene Expression in Spinal Muscular Atrophy Patients,' Eur J Hum Genet 13:256-259.
Brendan Lee et al, 'Blood ammonia and glutamine as predictors of hyperammonemic crises in patients with urea cycle disorder', Genetics in Medicine, US, (Dec. 11, 2014), vol. 17, No. 7, doi:10.1038/gim.2014.148, ISSN 1098-3600, pp. 561-568, XP055260189.
Brunetti-Pierri, N., et al., (2011) Phenylbutyrate Therapy for Maple Syrup Urine Disease, Hum Mol Genet 20(4):631-640.
Brusilow et al., Metabolism, vol. 42, No. 10 Oct. 1993, pp. 1336-1339, 'Restoration of Nitrogen Homeostasis in a Man with Ornithine Transcarbamylase Deficiency'.
Brusilow, S. W., 'Phenylacetylglutamine May Replace Urea as a Vehicle for Waste Nitrogen Excretion,' Ped. Res. 29(2):147-150(1991).
Brusilow, S.W. (1995). 'Urea Cycle Disorders: Clinical Paradigm of Hyperammonemic Enecphalopathy,' Chapter 12 in Progress in Liver Diseases pp. 293-309.
Brusilow, S.w. (Jun. 21, 1984). 'Treatment of Episodic Hyperammonemia in Children With Inborn Errors of Urea Synthesis,' N. Engl. J. Med. 310(25):1630-1634.
Brusilow, S.W. et al. (1995). 'Urea Cycle Enzymes,' Chapter 32 in the Metabolic and Molecular bases of Inherited Diseases, Scriver, C.R. et al. eds., McGraw-Hill, Inc. New York, pp. 1187-1232.
Brusilow, S.W., 'Protocols for Management of Intercurrent Hyperammonemia in Patients with Urea Cycle Disorders', FDA Application to Market a New Drug for Human Use or an Antibiotic Drug for Human Use, Fourteen pages (Amendment Dated Jul. 25, 1994).
Brusilow, S.W., et al. (Sep. 1, 1979) 'New Pathways of Nitrogen Excretion in Inborn Errors of Urea Synthesis,' Lancet 2(8140):452-454.
Brusilow, S.W., et al. (Feb. 8, 1980) 'Amino Acid Acylation: A Mechanism of Nitrogen Excretion in Inborn Errors of Urea Synthesis,' Science 207:659-661.
Brusilow, S.W., et al. (1991) 'Treatment of Urea Cycle Disorders,' Chapter 5 in Treatment of Genetic Diseases, Desnik, R.J. et al. eds, Churchill Livingstone, New York, New York, pp. 79-94.
Brusilow, S.W., et al. (1996) 'Urea Cycle Disorders: Diagnosis, Pathophysiology, and Therapy,' Adv Pediatr 43:127-170.
Burlina, A.B. et al., 'Long-Term Treatment with Sodium Phenylbutyrate in Ornithine Transcarbamylase-Deficient Patients', 72 Molecular Genetics and Metabolism 351-355 (2001).
Calloway, D.H. et al. (1971) 'Sweat and Miscellaneous Nitrogen Losses in Human Balance Studies,' J Nutrition 101:775-786.
Calloway, D.H. et al. (1971). 'Variation in Endogenous Nitrogen Excretion and Dietary Nitrogen Utilization as Determinants of Human Protein Requirements,' J. Nutrition 101:205-216.
Camacho, L.H. et al., Phase I Dose Escalation Clinical Trial of Phenylbutyrate Sodium Administered Twice Daily to Patients With Advanced Solid Tumors, 25 Invest. New Drugs 131-138 (2007, e-pub. Oct. 20, 2006).
Carducci, M., Phenylbutyrate Induces Apoptosis in Human Prostate Cancer and Is More Potent Than Phenylacetate, 2 Clinical Cancer Research 379-387 (1996).
Carducci, M.A. et al., A Phase I Clinical and Pharmacological Evaluation of Sodium Phenylbutyrate on an 120-h Infusion Schedule, 7 Clin. Cancer Res. 3047-3055 (2001).
Center for Drug Evaluation and Research, Clinical Pharmacology and Biopharmaceutics Review for New Drug Application No. 20-645 (Ammonul) (2005), 34 pgs.
Center for Drug Evaluation and Research, Labeling for New Drug Application No. 20-645 (Ammonul.RTM.) (2005).
Center for Drug Evaluation and Research, Medical Review for New Drug Application No. 20-645 (Ammonul) (2005), 55 pgs.
Chang J.-G., et al., 'Treatment of Spinal Muscular Atrophy by Sodium Butyrate,' PNAS USA (2001) 98(17):9808-9813.
Chang, C.-S.; Wu, P.-L. 'Synthesis of triglycerides of phenybutyric acid by lipase', J. Molecular Catalysis B: Enzymatic 61, 117-122 (2009).
Chang, C.-S.; Wu, P.-L. 'Synthesis of triglycerides of phenylalkanoic acids by lipase-catalyzed esterification in a solvent-free system', J. Biotech. 127, 694-702 (2007).
Chemical Abstract, vol. 116, No. 46308, Seiki et al, 'Homogenous Pharmaceutical Emulsions Containing Nonsteriodal Analogesics and Inflammation Inhibitors'. 1999.
Chemical Abstracts, vol. 112, No. 25, Jun. 18, 1990, (Columbus, Ohio, USA), p. 270, Abstract No. 231744t, Walsh J.P., "SN-1,2-Diacylglycerol Kinase of *Escherichia coli*. Diacylglycerol Analogs Define Specificity and Mechanism"; & Journal of Biological Chemistry, 1990, 265(8), (ENG).
Chen et al., 'Tributyrin: A Prodrug of Butyric Acid for Potential Clinical Applicaitn in Differentiation Therapy', Cancer Res., 54:3494-3499(1994).
Chung, Y.L., et al., (2000) "A Novel Approach for Nasopharyngeal Carcinoma Treatment Uese Phenylbutyrate as a Protein Kinase C Modulator: Implications for Radiosensitization and EBV-Targeted Therapy," Clin Cancer Res 6:1452-1458.
Clay, A. et. al, Hyperammonemia in the ICU, 132 Chest 1368-1378 (2007).
ClinicalTrials.Gov/Archive View of NCT00551200 on Dec. 11, 2007 'Dose-Escalation Safety Study of Glyceryl Tri (4-Phenylbutyrate)(GT4P) to Treat Urea Cycle Disorders' [accessed Oct. 5, 2009], 4 pages.
Collins, A.F. et al., Oral Sodium Phenylbutyrate Therapy in Homozygous Beta Thalassemia: A Clinical Trial, 85 Blood 43-49 (1995).
Combined Search and Examination Report dated Oct. 9, 2009 for Great Britain Patent Application No. GB0915545.8, filed on Aug. 27, 2009, eight pages.
Combined Search and Examination Report dated Sep. 9, 2010, for Great Britian Patent Application No. 1013468.2, filed on Aug. 27, 2009, six pages.
Complaint for Patent Infringement, *Horizon Therapeutics, Inc.* v. *Lupin Ltd. and Lupin Pharmaceuticals Inc.* Filed in U.S. District Court for the District of New Jersey, Oct. 19, 2015, 104 pgs.
Complaint for Patent Infringement, *Hyperion Therapeutics, Inc.* v. *Par Pharmaceuticals, Inc.* Filed in U.S. District Court for the Eastern District of Texas, Apr. 23, 20141 14 pgs.
Complaint, *Horizon Therapeutics, Inc.* v. *Lupin Ltd. et al.*; U.S. District Court for the District of New Jersey; Civ. Action No. 1:16-cv-00438-RBK-JS; Filed Jul. 21, 2016.
Complaint, *Horizon Therapeutics, Inc.* v. *Par Pharmaceutical, Inc.*; U.S. District Court for the District of New Jersey; Civ. Action No. 1:16-cv-03910-RBK-JS; Filed Jun. 30, 2016.
Comte, B. et al. (2002, e-pub. May 7, 2002). 'Identification of Phenylbutyrylglutamine, A New Metabolite of Phenylbutyrate Metabolism in Humans,' Journal of Mass Spectrometry 37(6):581-590.
Conn, H. O., et al., "Liver Physiology and Disease: Comparison of Lactulose and Neomycin in the Treatment of Chronic Portal-Systemic Encephalopathy. A Double Blind Controlled Trial," Gastroenterology 72(4):573-583 (1977).
Cordoba, J., "New assessment of hepatic encephalopathy"., Journal of Hepatology, (2011), vol. 54, p. 1030, 1032, 1038, XP028192163.
Cudkowicz (2009) Phase 2 Study of Sodium Phenylbutyrate in ALS,—Amyotrophic Lateral Sclerosis 10:99-106.

(56) References Cited

OTHER PUBLICATIONS

Darmaun, D. et al., 'Phenylbutyrate-Induced Glutamine Depletion in Humans: Effect on Leucine Metabolism', 5 Am. J. of Physiology: Endocrinology and Metabolism E801 (1998).

Darzens, G. et al.: 'Preparation de quelques glycerides phenylaliphatiques et leur reduction en alcools . . . ', Comptes Rendus Hebdomadaires Des Seances De L'Academie Des Sciences., vol. 205, Oct. 18, 1937, pp. 682-684.

Deferrari, G. et al. (1981). 'Brain Metabolism of Amino Acids and Ammonia in Patients with Chronic Renal Insufficiency,' Kidney International 20:505-510.

Diaz G.A.et al, 'Ammonia (NH3) control and improved neurocognitive outcome among urea cycle disorder (UCD) patients treated with glycerol phenylbutyrate (GPB).' Mol. Genet. Metab. 2012,105, 311, SIMD Abstract 24.

Diaz, G. A., et aL., Ammonia control anD Neurocognitive Outcome Among urea Cycle Disorder Patients Treated with Glycerol Phenylbutyrate, Hepatology 57(6):2171-2179 (2013).

Diaz, G.A., et al., 'Phase 3 Blinded, Randomized, Crossover Comparison of Sodium Phenylbutyrate (NaPBA) and Glycerol Phenylbutyrate (GPB): Ammonia (NH3) Control in Adults with Urea Cycle Disorders (UCDs),' Mol. Genet. Metab. 102:276, Society of Inherited Metabolic Disease (SMID) Abstract, (2011).

Dixon, M. A. and Leonard, J.V., Intercurrent Illness in Inborn Errors of Intermediary Metabolism, 67 Archives of Disease in Childhood, 1387-1391 (1992).

Dover, G. et al, Induction of Fetal Hemoglobin Production in Subjects with Sickle Cell Anemia by Oral Sodium Phenylbutyrate, 84(1) Blood 339-343.

Endo, F. et al., Clinical Manifestations of Inborn Errors of the Urea Cycle and Related Metabolic Disorders During Childhood, 134 J. Nutrition 1605S (2004).

Enns et al., 'Survival after Treatment with Phenylacetate and Benzoate for Urea-Cycle Disorders', N Engl J Med., vol. 356, No. 22, (May 31, 2007), pp. 2282-2292, URL: http://www.nejm.org, XP055148817.

European Medicines Agency, Annex I: Summary of Product Characteristics for Ammonaps, 1-33.

European Medicines Agency, European Public Assessment Report: Summary for the Public for Ammonaps (2009), 2 pgs.

European Medicines Agency, Scientific Discussion for Ammonaps (2005), 12 pgs.

European Medicines Agency, Scientific Discussion for Carbaglu (2004), 19 pgs.

European Patent Office, Extended European Search Report for EP09739263 completed Nov. 2, 2011, 6 pgs.

European Patent Office, International Search Report and Written Opinion for PCT/US2009/055256 completed Dec. 18, 2009 and dated Dec. 30, 2009, 13 pgs.

Examination Report for British Patent Application No. GB0915545.8 dated Oct. 27, 2010.

Examination Report for British Patent Application No. GB1013468.2 dated Oct. 28, 2011, 2 pgs.

Examination Report dated Feb. 5, 2010, for United Kingdom Patent Application No. GB0915545.8, filed on Aug. 27, 2009, two pages.

Examination Report dated May 11, 2010, for United Kingdom Patent Application No. GBO915545.8 filed on Aug. 27, 2009, one page.

FDA Label for Ammonul, sixteen pages {Feb. 2005).

FDA Label for Carbagiu, seven pages. (Mar. 2010).

FDA. 'Buphenyl (Sodium Phenylbutyrate) Label' nine pages (Aug. 2003).

FDA. (Jul. 2007). 'Label for Buphenyl,' 6 pages.

Feillet, F. and Leonard, J.V., Alternative Pathway Therapy for Urea Cycle Disorders, 21 J. Inher. Metab. Dis. 101-111 (1998).

Feoli-Fonseca, M. L., Sodium Benzoate Therapy in Children with Inborn Errors of Urea Synthesis: Effect on Carnitine Metabolism and Ammonia Nitrogen Removal, 57 Biochemical and Molecular Medicine 31-36 (1996).

Ferenci, P., et al., 'Hepatic EncephalopathyDefinition, Nomenclature, Diagnosis, and Quantification: Final Report of the Working Party at the 11th World Congresses of Gastroenterology, Vienna, 1998,' Hepatology 35:716-721 (2002).

Fernandes, Saudubray, Berghe (editors), 'Inborn Metabolic Diseases Diagnosis and Treatment', 219-222 (3d ed. 2000).

Gargosky, S. 'Improved Survival of Neonates Following Administration of Ammonul (Sodium Phenyl acetate & Sodium Benzoate) 10% 110% Injection', SSIEM Poster, six pages (Aug. 2, 2005).

Gargosky, S. et al., 'Results of a Twenty-two Year Clinical Irial: Acute, Adjunctive Pharmacological Treatment of Hyperammonemic Episodes in Patients with Deficiencies in Enzymes of the Urea Cycle', poster, Ucyclyd Pharma, Inc., one page (Oct. 14, 2005).

Gargosky, s., High Ammonia Levels Are Associated with Increased Mortality and Coma , Ucyclyd Pharma, Inc., one page (2006).

Geraghty, M.T. and Brusilow, S.W., Disorders of the Urea Cycle, in Liver Disease in Children 827-842 (F.J. Suchy et al., eds. 2001).

Ghabril, M. et al., Glycerol Phenylbutyrate (GPB) Administration in Patients with Cirrhosis and Episodic Hepatic Encephalopathy {HE), accepted for presentation at Digestive Disease Week (2012).

Ghabril, M., et al., 'Glycerol Phenylbutyrate in Patients With Cirrhosis and Episodic Hepatic Encephalopathy: A Pilot Study of Safety and Effect on Venous Ammonia Concentration,' Clinical Pharmacology in Drug Development 2 (3):278-284 (2013).

Gilbert, J. et al., A Phase I Dose Escalation and Bioavailability Study of Oral Sodium Phenylbutyrate in Patients with Refractory Solid Tumor Malignancies, 7 Clin. Cancer Research 2292-2300 (2001).

Gore, S. et al., 'Impact or the Putative Differentiating Agent sodium Phenylbutyrate on Myelodysplastic Syndromes and Acute Myeloid Leukemia', 7 Clin. Cancer Res. 2330 (2001).

Gropman, A. (2010) "Brain Imaging in Urea Cycle Disorders," Mol Genet Metab 100:S20-S30.

Gropman, A.L. et al. (2008) '1H MRS Identifies Symptomatic and Asymptomatic Subjects With Partial Ornithine Transcarbamylase Deficiency,' Mol. Genet. Metab. 95(1-2):21-30 (Sep.-Oct. 2008, e-pub. Jul. 26, 2008).

Gropman, A.L. et al., Neurological Implications of Urea Cycle Disorders, 30 J. Inherit Metab Dis. 865-879 (2007).

Gropman, A.L., et al., (2008) '1H MRS Allows Brain Phenotype Differentiation in Sisters with Late Onset Ornithine Transcarbamylase Deficiency (OTCD) and Discordant Clinical Presentations,' Mol Genet Metab 94(1):52-60.

Hassanein, T. I., et al., "Introduction to the Hepatic Encephalopathy Scoring Algorithm (HESA)," Dig. Dis. Sci. 53:529-538 (2008).

Hassanein, T. I., et al., "Randomized Controlled Study of Extracorporeal Albumin Dialysis for Hepatic Encephalopathy in Advanced Cirrhosis," Hepatology 46:1853-1862 (2007).

Hassanein, T., et al., 'Performance of the Hepatic Encephalopathy Scoring Algorithm in a Clinical Trial of Patients With Cirrhosis and Severe Hepatic Encephalopathy,' Am. J. Gastroenterol. 104:1392-1400 (2009).

Hines, P., et al., (2008) 'Pulsed-Dosing with Oral Sodium Phenylbutyrate Increases Hemoglobin F in a Patient with Sickle Cell Anemia,' Pediatr Blood Cancer 50:357-359.

Hogarth, P., et al., (2007) 'Sodium Phenylbutyrate in Huntington's Disease: A Dose-Finding Study,' Mov Disord 22(13):1962-1964.

Honda, S. et al., Successful Treatment of Severe Hyperammonemia Using Sodium Phenylacetate Power Prepared in Hospital Pharmacy, 25 Biol. Pharm. Bull. 1244-1246 (2002).

Huang, H.H., et al., (2012) "Cannabinoid Receptor 2 Agonist Ameliorates Mesenteric Angiogenesis and Portosystemic Collaterals in Cirrhotic Rats," Hepatology 56:248-258.

Hyperion Therapeutics. 'Hyperion Therapeutics Announces Enrollment of First Patient in Phase 1/2 Clinical Trial of GT4P in Patients with Urea Cycle Disorders' Announcement, 1 page (Oct. 23, 2007).

Hyperion Therapeutics. 'Hyperion Therapeutics Announces Results for Phase II Study in Urea Cycle Disorders,' located at <http://www.hyperiontx.com/press/release/pr1238518388,> last visited on Apr. 27, 2011, three pages (Mar. 30, 2009).

Hyperion Therapeutics. "Hyperion Therapeutics Announces Presentation of Long Term Data on Ammonia Control in Pediatric Patients

(56) References Cited

OTHER PUBLICATIONS

Treated with Ravicti® at the 12th International Congress of Inborn Errors of Metabolism and the Urea Cycle Disorder Satellite Symposium", Press Release, Sep. 3, 2013.
Hyperion Therapeutics. (Jun. 2, 2009.) Hyperion Therapeutics Announces Results of Phase I Study in Patients with Liver Cirrhosis, located at <http://www.hyperiontx.com/press/release/pr_1243891161>, last visited on Apr. 27, 2011, three pages.
International Preliminary Report on Patentability (Ch I) for PCT/US2012/028620 completed Jun. 4, 2012 and dated Apr. 10, 2014, 7 pgs.
International Preliminary Report on Patentability (Ch II) for PCT/US2012/028620, completed Aug. 22, 2013 and dated Sep. 4, 2013, 16 pgs.
International Preliminary Report on Patentability dated Mar. 1, 2011, for PCT Application No. PCT/US2009/030362, filed on Jan. 7, 2009, seven pages.
International Preliminary Report on Patentability dated Mar. 1, 2011, for PCT Application No. PCT/US2009/055256, filed on Aug. 27, 2009, six pages.
International Search Report and Written Opinion for PCT Application No. PCT/US09/30362, dated Mar. 2, 2009, filed on Jan. 7, 2009, 9 pages.
International Search Report and Written Opinion for PCT Application No. PCT/US2009/055256, dated Dec. 30, 2009, filed on Aug. 27, 2008, 13 pages.
IPR2015-01117, Inter Partes Review of U.S. Pat. No. 8,642,012, Petition, 186 pgs, Apr. 29, 2015.
IPR2015-01127, Inter Partes Review of U.S. Pat. No. 8,404,215 Petition Apr. 29, 2015.
James, M.O. et al. (1972). 'The Conjugation of Phenylacetic Acid in Man, Sub-Human Primates and Some Other Non-Primates Species,' Proc. R. Soc. London 182:25-35.
John, B.A., et al., 'The Disposition of HPN-100, A Novel Pharmaceutical Under Development for Potential Treatment of Hyperammonemia, in Cynomolgus Monkeys', ADMG 2009 ADME, poster, two pages (Mar. 2009).
John, Ba et al. (Mar. 2009). 'The Disposition of HPN-100, A Novel Pharmaceutical Under Development for Potential Treatment of Hyperammonemia, in Cynomologus Monkeys,' abstract presented at ACMG 2009, one page.
Jon P. R. Monteleone et al, 'Population Pharmacokinetic Modeling and Dosing Simulations of Nitrogen-Scavenging Compounds: Disposition of Glycerol Phenylbutyrate and Sodium Phenylbutyrate in Adult and Pediatric Patients with Urea Cycle Disorders', Journal of Clinical Pharmacology., US, (Jun. 15, 2013), vol. 53, No. 7, doi:10.1002/jcph.92, ISSN 0091-2700, pp. 699-710, XP055244763.
Kasumov, T. et al. (2004). 'New Secondary Metabolites of Phenylbutyrate in Humans and Rats,' Drug Metabolism and Disposition 32(1 ):10-19.
Khungar V et al, 'Management of Overt Hepatic Encephalopathy', Clinics in Liver Disease 2012 W.B. Saunders USA, (Feb. 2012), vol. 16, No. 1, ISSN 1089-3261, pp. 73-89, XP008179943.
Kleppe, S. et al., 'Urea Cycle Disorders', 5 Current Treatment Options in Neurology 309-319 (2003).
Kubota, K. and Ishizaki, T., Dose-Dependent Pharmacokinetics of Benzoic Acid Following Oral Administration of Sodium Benzoate to Humans, 41 Eur. J. Clin. Pharmacol. 363-368 (1991).
Lea et al., 'Butyramide and Monobutyrin: Growth Inhibitory and Differentiating Agents', Anticancer Res., 13: 145-150 (1993).
Lee, B. and Goss, J., Long-Term Correction of Urea Cycle Disorders, 138 J. Pediatrics S62-S71 (2001).
Lee, B. et al. (2009) 'Dosing and Therapeutic Monitoring of Ammona Scavenging Drugs and Urinary Phenylacetylglutamine (PAGN) as a Biomarker: Lessons From a Phase 2 Comparison of a Novel Ammonia Scavenging Agent with Sodium Phenylbutyrate (NAPBA),' presented at ICIEM 2009, San Diego, CA, poster, one page.
Lee, B. et al. (2009) 'Phase 2 Study of a Novel Ammonia Scavenging Agent in Adults With Urea Cycle Disorders (UCDs),' abstract presented at ACMG 2009, one page.
Lee, B. et al. (Aug. 2008). 'Preliminary Data on Adult Patients with Urea Cycle Disorders (UCD) in an Open-Label, Swirch-Over, Dose Escalation Study Comparing a New Ammonia Scavenger, Glyceryl Tri (4-Phenylbutyrate) [HPN-100], to Buphenyl (Sodium Phenylbutyrate [PBA])', abstract presented at SSSIEM 2008, Lisbon, Portugal, one page.
Lee, B. et al., "Phase 2 Study of a Novel Ammonia Scavenging Agent in Adults with Urea Cycle Disorders (UCDs)", presented at ACMG 2009, seventeen pages (Mar. 2009).
Lee, B. et al., "Preliminary Data on Adult Patients with Urea Cycle Disorders (UCD) in an Open-Label, Switch-Over, Dose Escalation Study Comparing a New Ammonia Scavenger, Glyceryl Tri (4-Phenylbutyrate) [HPN-100], to Buphenyl® (Sodium Phenylbutyrate [PBA])", presented at SSIEM 2008, Lisbon, Portugal, Poster, one page (Sep. 2008).
Lee, B. et al., Considerations in the Difficult-to-Manage Urea Cycle Disorder Patient, 21 Crit. Care Clin. S19-S25 (2005).
Lee, B., et al., 'Optimizing Ammonia (NH3) Control in Urea Cycle Disorder (UCD) Patients: A Predictive Model,' Oral Abstract Platform Presentations, Biochemical Genetics, Phoenix, AZ, Mar. 22, 2013, 2 pgs.
Lee, B., et al., 'Phase 2 Comparison of a Novel Ammonia Scavenging Agent with Sodium Phenylbutyrate in Patients with Urea Cycle Disorders: Safety, Pharmacokinetics and Ammonia Control,' Mol. Genet. Metab. 100(3):221-228 (2010).
Lee, B., et al., "Preliminary Data on Adult Patients with Urea Cycle Disorders (UCD) in an Open-Label, Switch-Over, Dose-Escalation Study Comparing a New Ammonia Scavenger, Glyceryl Tri(4-Phenylbutyrate) (HPN-100), to Buphenyl (Sodium Phenylbutyrate [PBA])", 31 J. Inherit. Metab. Dis. 91 (2008).
Leonard, J.V., Urea Cycle Disorders, 7 Semin. Nenatol. 27-35 (2002).
Levin, B. et al. "Hyperammonaemia: A Variant Type of Deficiency of Ornithinine Transcarbamylase." Arch. Dis. Childhd. 1969, 44, 162-169.
Lewis, H.B. (1914). 'Studies in the Synthesis of Hippuric Acid in the Animal Organism. II. The Synthesis and Rate of Elimination of Hippuric Acid After Benzoate Ingestion in Man,' J. Biol. Chem. 18:225-231.
Liang, K.Y., et al., 'Longitudinal Data Analysis Using Generalized Linear Models,' Biometrika 73(1):13-22 (1986).
Lichter-Konecki, U., et al., 'Ammonia Control in Children with Urea Cycle Disorders (UCDs); Phase 2 Comparison of Sodium Phenyl butyrate and Glycerol Phenylbutyrate,' Mol Genet Metab 103:323-329 (2011).
Lizardi-Cervera, J. et al, 'Hepatic Encephalopathy: A Review', 2 Annals of Hepatology 122-120 (2003).
MacArthur, R. B., et al., 'Pharmacokinetics of sodium phenylacetate and soium benzoate following intravenous administrtion as both a bolus and continuous infusion to healthy adult volunteers.' Mol Genet Metab 81 :(1 ):S67-S73 (2004).
Maestri NE, et al., Prospective treatment of urea cycle disorders. J Paediatr 1991 ;119:923-928.
Maestri, N.E. et al., 'Plasma Glutamine Concentration: A Guide in the Management of Urea Cycle Disorders', 121 J. Pediatrics 259 (1992).
Maestri, N.E., et al., Long-Term Survival of Patients with Argininosuccinate Synthetase Deficiency, 127 J. Pediatrics 929-935 (1993).
Maestri, N.E., Long-Term Treatment of Girls with Ornithine Transcarbamylase Deficiency, 355 N. Engl. J. Med. 855-859 (1996).
Majeed, K., Hyperammonemia, eMedicine.com (Dec. 2001), 12 pgs.
Mansour, A. et al. (Oct. 1997). 'Abdominal Operations in Patients with Cirrhosis: Still a Major Surgical Challenge,' Surqerv 122(4):730-735. (Abstract Only.).
Marini, J.C. et al., Phenylbutyrate Improves Nitrogen Disposal via an Alternative Pathway without Eliciting an Increase in Protein

(56) References Cited

OTHER PUBLICATIONS

Breakdown and Catabolism in Control and Ornithine Transcarbamylase-Deficient Patients, 93 Am. J. Clin. Nutr. 1248-1254 (2011).
Matsuda, I., Hyperammonemia in Pediatric Clinics: A Review of Ornithine Transcarbamylase Deficiency (OTCD) Based on our Case Studies, 47 JMAJ 160-165 (2004).
McGuire, B. et al. (2009) 'Pharmacokinetic (PK) and Safety Analyses of a Novel Ammonia-Reducing Agent in Healthy Adults and Patients with Cirrhosis,' abstract presented at DDW, two pages.
McGuire, B. et al. (2009) 'Pharmacokinetic (PK) and Safety Analyses of a Novel Ammonia-Reducing Agent in Healthy Adults and Patients with Cirrhosis,' Hyperion Therapeutics, poster, one page.
McGuire, B. et al., 'Pharmacokinetic <PK) Safety Study of Sodium Phenylacetate and Sodium Benzoate Administered to Subjects with Hepatic Impairment', abstract of the 13th International Symposium, Abano (Padova), Italy, Apr. 28-May 1, 2008, two pages (Apr. 2008).
McGuire, B. et al., "Pharmacokinetic Safety Study of Sodium Phenylacetate and Sodium Benzoate Administered to Subjects With Hepatic Impairments", 28 Liver International 743 (2008) (Abstract Only), 1 page.
McGuire, B. et al., (2010) 'Pharmacology and Safety of Glycerol Phenylbutyrate in Healthy Adults and Adults with Cirrhosis,' Hepatology 51:2077-2085.
McQuade, P.S., Analysis and the Effects of Some Drugs on the Metabolism of Phenylethylamine and Phenylacetic Acid, 8 Neuropsychopharmacol. Bio. Psychiat.607-614 (1984).
Mercuri, E, et al, (2004) 'Pilot Trial of Phenylbutyrate in Spinal Muscular Atrophy,' Neuromuscul Disord 14:130-135.
Mizutani, N. et al., Hyperargininemia: Clinical Course and Treatment with Sodium Benzoate and Phenylacetic Acid, 5 Brain and Development 555-563 (1983).
Mokhtarani et al., (2012) 'Urinary phenylacetylglutamine appears to be a more useful marker than metabolite blood levels for therapeutic monitoring of phenylacetic acid (PAA) prodrugs.' Mol Genet Metab 105, 341-342, SIMD Abstract 78.
Mokhtarani, M, et al, (2012) 'Elevated Phenylacetic Acid (PAA) Levels Appear Linked to Neurological Adverse Events in Healthy Adults but Not in Urea Cycle Disorder (UCD) Patients,' Mol Genet Metab 105:342.
Mokhtarani, M., et al., 'Elevated Phenylacetic Acid Levels do not Correlate with Adverse Events in Patients with Urea Cycle Disorders or Hepatic Encephalopathy and Can Be Predicted Based on the Plasma PAA to PAGN Ratio,' Mol. Genet. Metab. 110(4):446-53 (2013).
Mokhtarani, M., et al., 'Urinary Phenylacetylglutamine as Dosing Biomarker for Patients with Urea Cycle Disorders,' Mol. Genet. Metab. 107(3):308-314 (2012).
Moldave, K, et al, (1957) 'Synthesis of Phenylacetylglutamine by Human Tissue,' J. Biol. Chem. 229:463-476.
Monteleone, JPR, et al., (2012) 'Population pk Analysis of Glycerol Phenylbutyrate (GPB) and Sodium Phenylbutyrate(NAPBA) in Adult and Pediatric Patients with Urea Cycle Discarders,' Mol Genet Metab 105:343-344.
Munoz, S. J, 'Hepatic Encephalopathy,' Med. Clin. N. Am. 92:795-812 (2008).
Nassogne, M.C., Urea Cycle Defects: Management and Outcome, 28 J. Inherit. Metab. Dis. 407 (2005), 407-414.
New England Consortium of Metabolic Programs, Acute Illness Protocol: Urea Cycle Disorders: The Infant/Child with Argininosuccinate Lyase Deficiency, adapted from Summar, M and Tuchman, M, Proceedings of a Consensus Conference for the Management of Patients with Urea Cycle Disorders, 138 J. Peds. Suppl. (2001), 7 pgs.
New England Consortium of Metabolic Programs, Acute Illness Protocol: Urea Cycle Disorders: The Infant/Child with Citrullinemia, adapted from Summar, M and Tuchman, M, Proceedings of a Consensus Conference for the Management of Patients with Urea Cycle Disorders, 138 J. Peds. Suppl. (2001), 7 pgs.

Newmark et al., 'Butyrate and Phenylacetate as Differentiating Agents: Practical Problems and Opportunities', Jour. of Cell. Biochem., Supplement 22: 247-253(1995).
Ong, J. P., et al., (2003) 'Correlation Between Ammonia Levels and the Severity of Hepatic Encephalopathy,' Am. J. Med. 114:188-193.
Ortiz, M., et al., "Development of a Clinical Hepatic Encephalopathy Staging Scale," Aliment Pharmacol Ther 26:859-867 (2007).
PAR Pharmaceutical, Inc.s Initial Invalidity Contentions and Non-Infringement Contentions for U.S. Pat. No. 8,404,215 and U.S. Pat No. 8,642,012, Nov. 13, 2014, 93. Pgs.
Parsons-Smith, B. G., et al., "The Electroencephalograph in Liver Disease," Lancet 273:867-871 (1957).
Perrine, S. P., (2008) 'Fetal Globin Stimulant Therapies in the Beta-Hemoglobinopathies: Principles and Current Potential,' Pediatr Ann 37(5):339-346.
Phuphanich, S. et al., Oral Sodium Phenylbutyrate in Patients with Recurrent Malignant Gliomas: A Dose Escalation and Pharmacologic Study, Neuro-Oncology 177 (2005).
Piscitelli, S.C. et al. (1995). 'Disposition of Phenyl butyrate and its Metabolites, Phenylacetete and Phenylacetylglutamine,' J. Clin. Pharmacal. 35:368-373.
Praphanproj, V. et al., Three Cases of Intravenous Sodium Benzoate and Sodium Phenylacetate Toxicity Occurring in the Treatment of Acute Hyperammonemia, 23 J. Inherited Metabolic Disease 129-136 (2000).
Propst, A. et al, 'Prognosis and Lite Expectancy in Chronic Liver Disease', 40 Dig Dis Sci 1805 (1995) (Abstract Only).
Riley, T.R. et al. (Nov. 15, 2001). 'Preventive Strategies in Chronic Liver Disease: Part II. Cirrhosos,' Am. Fam. Physician 64(10):1735-1740. (Abstract Only).
Rockey, D. C., et al., 'Randomized, Controlled, Double Blind Study of Glycerol Phenylbutyrate in Patients with Cirrhosis and Episodic Hepatic Encephalopathy,' Hepatology 56:248(A) (2012), 1 pge.
Rudman, D., et al., Maximal Rates of Excretion and Synthesis of Urea in Normal and Cirrhotic Subjects, 52 J. Clin. Invest. 2241-2249 (1973).
Ryu, H, et al, (2005) 'Sodium Phenylbutyrate Prolongs Survival and Regulates Expression of Anti-Apoptotic Genes in Transgenic Amyotrophic Lateral Sclerosis Mice,' J Neurochem 93:1087-1098.
Salam, M, et al, 'Modified-Orientation Log to Assess Hepatic Encephalopathy,' Aliment Pharmacol Ther. 35(8):913-920 (2012).
Scientific Discussion for Ammonaps, EMEA 2005, available at http://www.ema.europa.eu/docs/enGB/document_library/EPAR-ScientificDiscussion/human/000219/WC500024748.pdf, 12 pgs.
Scottish Medicines Consortium, Carglumic Acid 200 mg Dispersible Tablets (Carbaglu) No. 299/06 (Sep. 8, 2006), 5 pgs.
Seakins, J.W.T., The Determination of Urinary Phenylacetylglutamine as Phenylacetic Acid: Studies on its Origin in Normal Subjects and Children with Cystic Fibrosis, 35 Clin. Chim. Acta.121-131 (1971).
Search and Examination Report for British Patent Application No. GB 0915545.8, dated Oct. 8, 2009, 5 pages.
Sherwin, C. et al., The Maximum Production of Glutamine by the Human Body as Measured by the Output of Phenylacetylglutamine, 37 J. Biol. Chem. 113(1919).
Shiple, G.J. et al., Synthesis of Amino Acids in Animal Organisms. I. Synthesis of Glycocoll and Glutamine in the Human Organism, 44 J. Am. Chem. Soc. 618-624 (1922).
Simell, O et al: 'Waste nitrogen excretion via amino acid acylation: Benzoate and phenylacetate in lysinuric protein intolerance' Pediatric Research, Williams and Wilkins, Baltimore, MD, US, vol. 20, No. 11, Jan. 1, 1986 (Jan. 1, 1986), pp. 1117-1121, XP009127277 ISSN: 0031-3998.
Singh, "Consensus Statement from a Conference for the Management of Patients with Urea Cycle Disorders", 138 J. Pediatrics S1-S5 (2001).
Smith, W., et al., "Ammonia Control in Children Ages 2 Months through 5 Years with Urea Cycle Disorders: Comparison of Sodium Phenylbutyrate and Glycerol Phenylbutyrate," J Pediatr. 162(6):1228-1234.e1 (2013).
South San et al, 'Hyperion Therapeutics Announces Presentation of Long Term Data on Ammonia Control in Pediatric Patients Treated With RAVICTI(R) at the 12th International Congress of Inborn

(56) References Cited

OTHER PUBLICATIONS

Errors of Metabolism and the Urea Cycle Disorder Satellite Symposium', (Sep. 3, 2013), URL: http://files.shareholder.com/downloads/AMDA-1412CE/0x0x688110/4e684e9d-6c54-4963-a993-72c90f308802/HPTX_News_2013_9_3_General_Releases.pdf, (Mar. 21, 2016), XP055260208.

Stauch et al., 'Oral L-ornithine-L-aspartate therapy of chronic hepatic encephalopathy: results of a placebo-controlled double-blind study', Journal of Hepatology, vol. 28, No. Issue, (May 1998), pp. 856-864, URL: http://www.sciencedirect.com, XP055250053.

Summar, M. and Tuchman, M., Proceedings of a Consensus Conference for the Management of Patients with Urea Cycle Disorders, 138 J. Pediatrics S6-S10 (2001).

Summar, M. et al., 'Description and Outcomes of 316 Urea Cycle Patients From a 21-Year, Multicenter Study of Acute Hyperammonemic Episodes', Abstract, presented at Annual Symposium CCH-Congress Centre Hamburg, Sep. 4-7, 2007, GSSIEM 2007, two pages.

Summar, M. et al., Unmasked Adult-Onset Urea Cycle Disorders in the Critical Care Setting, 21 Crit. Care Clin. S1-S8 (2005).

Summar, M., Current Strategies for the Management of Neonatal Urea Cycle Disorders, 138 J. Pediatrics S30-S39 (2001).

Summar, M., Urea Cycle Disorders Overview, Gene Reviews, www.genetests.org (Apr. 2003), 15 pgs.

Summar, M.L. et al., Diagnosis, Symptoms, Frequency and Mortality of 260 Patients with Urea Cycle Disorders From a 21-Year, Multicentre Study of Acute Hyperammonemic Episodes, 97 Acta Paediatr. 1420-1425 (Oct. 2008, e-pub. Jul. 17, 2008).

Sushma, S. et al., 'Sodium Benzoate in the Treatment of Acute Hepatic Encephalopathy: A Randome Double-blind Trial,' Hepatology, 16 (1992), 138-144.

Swedish Orphan International, 'Urea Cycle Disorders an International Perspective', Poster, Symposium Swedish Orphan International, Barcelona, Spain, Jan. 12, 2007, one page. (2007).

Tanner, L. M., et al., Nutrient Intake in Lysinuric Protein Intolerance, 30 J. Inherit. Metab. Dis. 716 (2007), 716-721.

The National Organization for Rare Disorders (2012). The Physician's Guide to Urea Cycle Disorders, at http://nordphysicianguides.org/wp-content/uploads/2012/02/NORD_Physician_Guide_to_Urea_Cycle_Disorders.pdf, 28 pgs.

Thibault, A., et al., 'A Phase I and Pharmacokinetic Study of Intravenous Phenylacetate in Patients with Cancer,' Cancer Res. 54:1690-1694 (1994).

Thibault, A., et al., 'Phase I Study of Phenylacetate Administered Twice Daily to Patients with Cancer,' Cancer 75:2932-2938 (1995).

Thompson, P. 'Pharmacokinetics of phenyacetate administered as a 30-min infusion in children with refractory cancer', Cancer Chemother. Pharmacol. 2003, 52: 417-423.

Todo, S. et al., Orthotopic Liver Transplantation for Urea Cycle Enzyme Deficiency, 15 Hepatology 419-422 (1992).

Tuchman, M. et al. (2008, e-pub. Jun. 17, 2008). 'Cross-Sectional Multicenter Study of Patients With Urea Cycle Disorders in the United States,' Malec. Genetics Metab. 94:397-402.

Tuchman, M., and Yudkoff, M., Blood Levels of Ammonia and Nitrogen Scavenging Amino Acids in Patients with Inherited Hyperammonemia, 66 Molecular Genetics and Metabolism 10-15 (1999).

UMass Memorial Medical Center, Lab Updates, 'Measurement of Ammonia in Blood.' Feb. 2007. Accessed at www.ummlabs.org/News/07Feb.pdf, 3 pgs.

United States Patent and I rademark Office, International Search Report and Written Opinion lor PCT/ US2014/060543 dated Jan. 23, 2015.

United States Patent and Trademark Office, International Search Report and Written Opinion dated Jan. 16, 2015 for PCT/US14/58489, 8 pgs.

United States Patent and Trademark Office, International Search Report and Written Opinion dated Jun. 4, 2012 for PCT/US2012/028620.

United States Patent and Trademark Office, International Search Report and Written Opinion for PCT/US2009/030362, dated Mar. 2, 2009, 9 pgs.

United States Patent and Trademark Office, International Search Report and Written Opinion for PCT/US2012/54673 dated Nov. 20, 2012, 8 pgs.

United States Patent and Trademark Office, International Search Report and Written Opinion for PCT/US2013/71333 dated Mar. 28, 2014, 9 pgs.

Vilstrup, H, et al, 'Hepatic Encephalopathy in Chronic Liver Disease: 2014 Practice Guideline by the American Association for the Study of Liver Diseases and the European Association for the Study of the Liver,' Hepatology 60 (2):715-735 (2014).

Walsh et al., Chemical Abstract vol. 112, No. 231744, 1990, 1 pge.

Walsh et al., The Journal of Biological Chemistry, vol. 265, No. 8, pp. 4374-4381 (1990), sn-1,2-Diacylgylcerol Kinase of *Escherichia coli*.

Waterlow, J.C., The Partition of Nitrogen in the Urine of Malnourished Jamaican Infants, 12 Am. J. of Clin. Nutrition 235-240 (1963).

Welbourne, T. et al., 'The Effect of Glutamine Administration on Urinary Ammonium Excretion in Normal Subjects and Patients with Renal Disease', 51 J. Clin. Investigation 1852 {1972).

Wilcken, B, 'Problems in the Management of Urea Cycle Disorders', 81 Molecular Genetics and Metabolism 85 (2004).

Wilson, C.J, et al, 'Plasma Glutamine and Ammonia Concentrations in Ornithine Carbamoyltransferase Deficiency and Citrullinaemia', 24 J. Inherited Metabolic Disease 691 (2001).

Wright, G., et al., Management of Hepatic Encephalopathy, 2011 International Journal of Hepatology 1 (2011), 11 pgs.

Wright, P., Review: Nitrogen Excretion: Three End Products, Many Physiological Roles, 198 J. Experimental Biology 273-281 (1995).

Xie, G, et al, (2012) 'Role of Differentiation of Liver Sinusoidal Endothelial Cells in Progression and Regression of Hepatic Fibrosis in Rats,' Gastroenterology 142:S918.

Yajima, et al. 'Diurnal Fluctuations of Blood Ammonia Levels in Adult-Type Citrullinemia', 137 Tokohu J. Ex/ Med, 213-220 (1982).

Yu, Ryan and Potter, Murray, 'Diagnosis of Urea Cycle Disorders in Adulthood: Late-Onset Carbamyl Phosphate Synthetase 1 Deficiency', 7 MUMJ 30 (2010).

Yudkoff, M. et al., In Vivo Nitrogen Metabolism in Ornithine Transcarbamylase Deficiency, 98 J. Clin. Invest. 2167-2173 (1996).

Zeitlin, P., Novel Pharmacologic Therapies for Cystic Fibrosis, 103 J. Clinical Investigation 447 (1999).

Zeitlin, P.L. et al. (2002) 'Evidence of CFTR Function in Cystic Fibrosis After System Administration of 4-Phenylbutyrate,' Mol Therapy 6(1 ):119-126.

Complaint, *Horizon Therapeutics, Inc.* v. *Lupin Ltd. et al.*; U.S. District Court for the District of New Jersey; Civ. Action No. 2:17-cv-05900-KM-MAH; Filed Aug. 8, 2017.

Complaint, *Horizon Therapeutics, Inc.* v. *Par Pharmaceutical, Inc.*; U.S. District Court for the District of New Jersey; Civ. Action No. 2:17-cv-05901-KM-MAH; Filed Aug. 8, 2017.

Doi, et al., "Development of an Azanoradamantane-Type Nitroxyl Radical Catalyst for Class-Selective Oxidation of Alcohols," J Org Chem 80 (1), 401-413. Dec. 16, 2014.

Fey, et al., "Silica-Supported TEMPO Catalysts: Synthesis and Application in the Anelli Oxidation of Alcohols," J. Org. Chem., 2001, 66 (24), pp. 8154-8159.

Shibuya, et al, "Nitroxyl Radical/Phl(OAc)2: One-Pot Oxidative Cleavage of Vicinal Diols to (Di)Carboxylic Acids," 2012, Org. Lett., vol. 14, No. 19, pp. 5010-5013.

Zhao, et al., "Oxidation of Primary Alcohols to Carboxylic Acids with Sodium Chlorite Catalyzed by TEMPO and Bleach," J. Org. Chem., 1999, 64 (7), pp. 2564-2566.

Uribe, M. et al., "Hyperammonemic Hepatic Encypholopathy Treated with Sodium Benzoate, Final report of double blind evaluation", Instituto Nacional de la Nutricion, Mexico D.F., Hepatology, 10(4):589, (1989).

Koya, Toshinari et al., Poster Session, Liver P-397, A study of administration of granular preparations of branched chain amino acids during transcatheter arterial chemoembolisation for hepatocellular carcinoma, Department of Gastrointestinal Medicine, Anjo Kosei Hospital, 2017, p. A775.

(56) References Cited

OTHER PUBLICATIONS

Nagazumi Atsushi et al., Use experience of Monilac for hepatic encephalopathy, Journal of New Remedies & Clinics, vol. 24, No. 8, Aug. 1975, pp. 1271-1274 41-44.
Smith, W. et al., Ammonia (NH3) Control in Children Ages 2 Months through 5 Years with Urea Cycle Disorders (UCDs): Comparison of Sodium Phenylbutyrate and Glycerol Phenylbutyrate, Poster Abstract 774W from American Society of Human Genetics 62nd Annual Meeting, Nov. 6-10, 2012, San Francisco, CA.
Lindquist and Hernell, Curr Opin Clin Nutr Metab Care 13: 314-320, 2010.
Mas et al., Biochem J. 289: 609-615, 1993.
Mas et al., Methods Enzymol. 284: 340-353, 1997.
Ruvoen-Clouet et al., Biochem J. 393: 627-634, 2006.
Sias et al., Biochemistry 43: 10138-10148, 2004.
Eydoux et al., J. Lipid. Res. 48: 1539-1549, 2007.
Amara et al., Biochim. Biophys. Acta 1791: 983-990, 2009.
Xiao et al., J Biol Chem. 286(30): 26353-26363, 2011.
Berry et al., Mol. Gen. and Metab. 122: 46-53, 2017.
Andersson et al., Biochim. Biophys. Acta 1302: 236-240, 1996.
Berry et al., Poster titled "Pharmacokinetics of glycerol phenylbutyrate in pediatric patients 2 months to 2 years of age with urea cycle disorder" presented at American Society of Human Genetics Meeting, Oct. 17-21, 2017.
NCT00947297, Clinical Trial.gov archive, May 3, 2011.
McGuire et al, Hepatology Jun. 2010; 51(6): 2077-2085.
MedCalc: Body Surface Area, Body Mass Index (BMI), Jan. 15, 2000.
Ammonul Product Specification, Cangene Biopharma Inc. Feb. 2005.
Lee, B. et al. (2009) 'Dosing and Therapeutic Monitoring of Ammona Scavenging Drugs and Urinary Phenylacetylglutamine (PAGN) as a Biomarker: Lessons From a Phase 2 Comparison of a Novel Ammonia Scavenging Agent with Sodium Phenylbutyrate (NAPBA),' "abstract" presented at ICIEM 2009, San Diego, CA, poster, one page.
Yurdaydin C., Blood ammonia determination in cirrhosis: Still confusing after all these years? Hepatology 38 (5) Nov. 2003, pp. 1307-1310.
Häberle J etal., Suggested guidelines for the diagnosis and management of urea cycle disorders, Orphanet J Rare Dis. May 29, 2012;7:32.
Vierling JM etal., Fasting Blood Ammonia Predicts Risk and Frequency of Hepatic Encephalopathy Episodes in Patients With Cirrhosis, Clin Gastroenterol Hepatol. Jun. 2016;14(6):903-906.
Rose CF, Ammonia-lowering strategies for the treatment of hepatic encephalopathy, Clin Pharmacol Ther. Sep. 2012;92(3):321-31.
Berry SA et al., Glycerol phenylbutyrate treatment in children with urea cycle disorders: pooled analysis of short and long-term ammonia control and outcomes, Mol Genet Metab. May 2014;112(1):17-24.

METHODS OF THERAPEUTIC MONITORING OF NITROGEN SCAVENGING DRUGS

RELATED APPLICATIONS

The present application is a continuation of U.S. patent application Ser. No. 15/687,132, filed Aug. 25, 2017, which is a continuation of U.S. patent application Ser. No. 15/457,643, filed Mar. 13, 2017, which is a continuation of U.S. patent application Ser. No. 15/074,691, filed Mar. 18, 2016, which is a continuation of U.S. patent application Ser. No. 14/958,259, filed Dec. 3, 2015, now U.S. Pat. No. 9,326,966, which is a continuation of Ser. No. 14/816,674, filed Aug. 3, 2015, now U.S. Pat. No. 9,254,278, which is a continuation of Ser. No. 13/775,000, filed Feb. 22, 2013, now U.S. Pat. No. 9,095,559, which is a divisional of U.S. patent application Ser. No. 13/417,137, filed Mar. 9, 2012, now U.S. Pat. No. 8,404,215, which claims the benefit of U.S. Provisional Application No. 61/564,668, filed Nov. 29, 2011, and U.S. Provisional Application No. 61/542,100, filed Sep. 30, 2011, the disclosures of which are incorporated by reference herein in their entirety, including drawings.

BACKGROUND

Nitrogen retention disorders associated with elevated ammonia levels include urea cycle disorders (UCDs) and hepatic encephalopathy (HE).

UCDs include several inherited deficiencies of enzymes or transporters necessary for the synthesis of urea from ammonia, including enzymes involved in the urea cycle. The urea cycle is depicted in FIG. 1, which also illustrates how certain ammonia-scavenging drugs act to assist in elimination of excessive ammonia. With reference to FIG. 1, N-acetyl glutamine synthetase (NAGS)-derived N-acetylglutamate binds to carbamyl phosphate synthetase (CPS), which activates CPS and results in the conversion of ammonia and bicarbonate to carbamyl phosphate. In turn, carbamyl phosphate reacts with ornithine to produce citrulline in a reaction mediated by ornithine transcarbamylase (OTC). A second molecule of waste nitrogen is incorporated into the urea cycle in the next reaction, mediated by arginosuccinate synthetase (ASS), in which citrulline is condensed with aspartic acid to form argininosuccinic acid. Argininosuccinic acid is cleaved by argininosuccinic lyase (ASL) to produce arginine and fumarate. In the final reaction of the urea cycle, arginase (ARG) cleaves arginine to produce ornithine and urea. Of the two atoms of nitrogen incorporated into urea, one originates from free ammonia ($NH_4^+$) and the other from aspartate. UCD individuals born with no meaningful residual urea synthetic capacity typically present in the first few days of life (neonatal presentation). Individuals with residual function typically present later in childhood or even in adulthood, and symptoms may be precipitated by increased dietary protein or physiological stress (e.g., intercurrent illness).

Hepatic encephalopathy (HE) refers to a spectrum of neurologic signs and symptoms believed to result from hyperammonemia, which frequently occur in subjects with cirrhosis or certain other types of liver disease. Subjects with HE typically show altered mental status ranging from subtle changes to coma, features similar to subjects with UCDs.

Subjects with nitrogen retention disorders whose ammonia levels and/or symptoms are not adequately controlled by dietary restriction of protein and/or dietary supplements are generally treated with nitrogen scavenging agents such as sodium phenylbutyrate (NaPBA, approved in the United States as BUPHENYL® and in Europe as AMMONAPS®) or sodium benzoate. These are often referred to as alternate pathway drugs because they provide the body with an alternate pathway to urea for excretion of waste nitrogen (Brusilow 1980; Brusilow 1991). NaPBA is a phenylacetic acid (PAA) prodrug. Another nitrogen scavenging drug currently in development for the treatment of nitrogen retention disorders is glyceryl tri-[4-phenylbutyrate](HPN-100), which is described in U.S. Pat. No. 5,968,979. HPN-100, which is commonly referred to as GT4P or glycerol PBA, is a prodrug of PBA and a pre-prodrug of PAA.

HPN-100 and NaPBA share the same general mechanism of action: PBA is converted to PAA via beta oxidation, and PAA is conjugated enzymatically with glutamine to form phenylacetylglutamine (PAGN), which is excreted in the urine. The structures of PBA, PAA, and PAGN are set forth below.

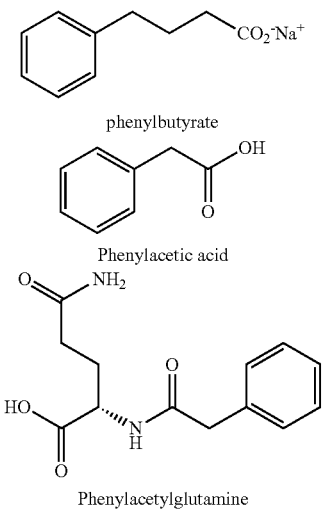

The clinical benefit of NaPBA and HPN-100 with regard to nitrogen retention disorders derives from the ability of PAGN to effectively replace urea as a vehicle for waste nitrogen excretion and/or to reduce the need for urea synthesis (Brusilow 1991; Brusilow 1993). Because each glutamine contains two molecules of nitrogen, the body rids itself of two waste nitrogen atoms for every molecule of PAGN excreted in the urine. Therefore, two equivalents of nitrogen are removed for each mole of PAA converted to PAGN. PAGN represents the predominant terminal metabolite, and one that is stoichiometrically related to waste nitrogen removal, a measure of efficacy in the case of nitrogen retention states. The difference between HPN-100 and NaPBA with respect to metabolism is that HPN-100 is a triglyceride and requires digestion, presumably by pancreatic lipases, to release PBA (McGuire 2010).

In contrast to NaPBA or HPN-100, sodium benzoate acts when benzoic acid is combined enzymatically with glycine to form hippuric acid. For each molecule of hippuric acid excreted in the urine, the body rids itself of one waste nitrogen atom.

Methods of determining an effective dosage of PAA prodrugs such as NaPBA or HPN-100 for a subject in need of treatment for a nitrogen retention disorder are described in WO09/1134460 and WO10/025303. Daily ammonia levels, however, may vary greatly in a subject. This can lead to overestimation by the physician of the average daily ammonia levels, which may result in overtreatment. Thus, there is a need in the art for improved methods for PAA prodrug dose determination and adjustment based on ammonia levels in subjects with nitrogen retention disorders such as UCDs or HE.

SUMMARY

Provided herein in certain embodiments are methods for determining whether to increase a dosage of a nitrogen scavenging drug in a subject with a nitrogen retention disorder by measuring a fasting blood ammonia level and comparing the fasting blood ammonia level to the upper limit of normal (ULN) for blood ammonia, where a fasting blood ammonia level that is greater than half the ULN for blood ammonia indicates that the dosage needs to be increased. In certain embodiments, the nitrogen retention disorder is a UCD or HE. In certain embodiments, the nitrogen scavenging drug is HPN-100, PBA, NaPBA, sodium benzoate, or any combination thereof (i.e., any combination of two or more of HPN-100, PBA, NaPBA). In certain embodiments, the ULN is around 35 µmol/L or 59 µg/mL. In certain embodiments, the methods include an additional step of administering an increased dosage of the nitrogen scavenging drug if the need exists, and in certain of these embodiments administration of the nitrogen scavenging drug produces a normal average daily ammonia level in the subject. In certain embodiments wherein a determination is made to administer an increased dosage of nitrogen scavenging drug and wherein the nitrogen scavenging drug is a PAA prodrug, the methods include an additional step of measuring urinary PAGN excretion and determining an effective dosage of the PAA prodrug based on a mean conversion of PAA prodrug to urinary PAGN of 60-75%.

Provided herein in certain embodiments are methods for determining whether to administer a nitrogen scavenging drug to a subject with a nitrogen retention disorder by measuring a fasting blood ammonia level and comparing the fasting blood ammonia level to the ULN for blood ammonia, where a fasting blood ammonia level that is greater than half the ULN for blood ammonia indicates that the nitrogen scavenging drug needs to be administered. In certain embodiments, the nitrogen retention disorder is a UCD or HE. In certain embodiments, the nitrogen scavenging drug is HPN-100, PBA, NaPBA, sodium benzoate, or any combination thereof (i.e., any combination of two or more of HPN-100, PBA, NaPBA). In certain embodiments, the ULN is around 35 µmol/L or 59 µg/mL. In certain embodiments, the methods include an additional step of administering a nitrogen scavenging drug if the need exists, and in certain of these embodiments administration of the nitrogen scavenging drug produces a normal average daily ammonia level in the subject. In certain embodiments wherein a determination is made to administer a nitrogen scavenging drug and wherein the nitrogen scavenging drug is a PAA prodrug, the methods further include a step of determining an effective initial dosage of the PAA prodrug by determining a target urinary PAGN output based on a target nitrogen output and calculating an effective initial dosage that results in the target urinary PAGN output based on a mean conversion of PAA prodrug to urinary PAGN of 60-75%. In certain embodiments, the methods include a step of administering the calculated effective initial dosage.

Provided herein in certain embodiments are methods for treating a nitrogen retention disorder in a subject who has previously been administered a nitrogen scavenging drug by measuring a fasting blood ammonia level, comparing the fasting blood ammonia level to the ULN for blood ammonia, and administering an increased dosage of the nitrogen scavenging drug if the fasting ammonia level is greater than half the ULN for blood ammonia. In certain embodiments, administration of an increased dosage of the nitrogen scavenging drug produces a normal average daily ammonia level in the subject. In certain embodiments, the nitrogen retention disorder is a UCD or HE. In certain embodiments, the nitrogen scavenging drug is HPN-100, PBA, NaPBA, sodium benzoate, or any combination thereof (i.e., any combination of two or more of HPN-100, PBA, NaPBA). In certain embodiments, the ULN is around 35 µmol/L or 59 µg/mL. In certain embodiments wherein the nitrogen scavenging drug is a PAA prodrug, the methods include an additional step of measuring urinary PAGN excretion and determining an effective dosage of the PAA prodrug based on a mean conversion of PAA prodrug to urinary PAGN of 60-75%. In certain embodiments, the methods include a step of administering the calculated effective dosage.

DETAILED DESCRIPTION

Figure 1:
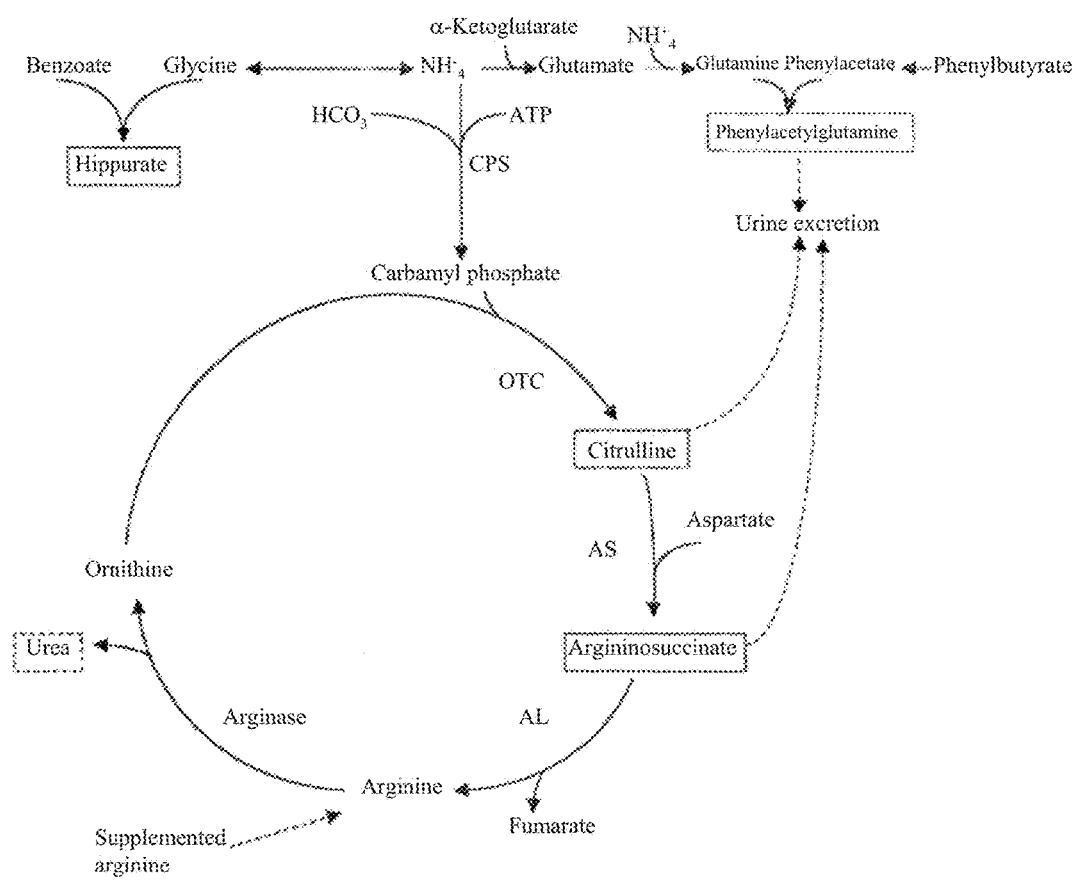
FIG. 1: The urea cycle and how certain nitrogen-scavenging drugs may assist in elimination of excessive ammonia.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

In subjects with a nitrogen retention disorder, the desired effect of treatment with a nitrogen scavenging drug is control of blood ammonia level. Control of blood ammonia level generally refers to ammonia values within the normal range and avoidance of hyperammonemic crises, which are often defined in the art as transient ammonia values exceeding 100 µmol/L or 178 µg/mL accompanied by clinical signs and symptoms of hyperammonemia. Dosing of nitrogen scavenging drugs is usually based upon clinical assessment and measurement of ammonia. However, assessment of treatment effect and interpretation of ammonia levels is confounded by the fact that individual ammonia values vary several-fold over the course of a day and are impacted by timing of the blood draw in relation to the last meal and dose of drug (see, e.g., Lee 2010; Lichter-Konecki 2011; Diaz 2011).

A random ammonia value obtained during an outpatient visit may fail to provide a reliable measure of a subject's status and the drug effect. For example, basing treatment on a blood sample taken after eating a meal might overestimate average daily ammonia level and result in overtreatment. Conversely, basing treatment on a blood sample taken after drug administration might underestimate average daily ammonia level and result in undertreatment. A fasting ammonia level at or near the ULN might be taken as an indication of satisfactory control without appreciating the fact that the ammonia burden during the day (average and/or highest possible value) might be significantly higher. Thus, a fasting level at or near the ULN may actually reflect undertreatment in a subject already a receiving nitrogen scavenging drug or the need for treatment in a subject not currently prescribed a nitrogen scavenging drug. A more accurate view of daily ammonia level could be obtained by multiple blood draws in a controlled setting over an extended period of time. Although this is currently done in clinical trials, it is clinically impractical.

As set forth below, the relationship between fasting ammonia levels and daily ammonia exposure was evaluated in subjects with nitrogen retention disorders. It was found that fasting ammonia correlates strongly with daily ammonia exposure, assessed as a 24 hour area under the curve for ammonia, daily average, or maximal daily concentration, and that a target fasting value which does not exceed half of the ULN is a clinically useful and practical predictor of ammonia values over 24 hours. As such, provided herein are clinically practical methods of evaluating ammonia exposure in subjects with nitrogen retention disorders based on fasting ammonia levels, as well as methods of using the resultant information to adjust the dosage of a nitrogen scavenging drug, determine whether to administer a nitrogen scavenging drug, treat a nitrogen retention disorder, and predict daily ammonia burden. The use of fasting ammonia levels to predict ammonia exposure provides a significant advantage over previously developed methods by reducing the number of required blood draws and eliminating the confusion associated with conflicting ammonia levels over the course of the day.

As further disclosed herein, the relationship between ammonia control and neurocognitive outcome was evaluated in UCD patients. Previous research has demonstrated that UCD patients often exhibit lower IQ overall and deficient executive function manifested by difficulty in goal setting, planning, monitoring progress and purposeful problem solving. As set forth herein, it was found that ammonia control with GPB resulted in a significant improvement in executive functions in pediatric patients. Based on these results, methods are provided herein for improving executive function in a pediatric subject with a UCD by administering one or more nitrogen scavenging drugs.

As further disclosed herein, the relationship between elevated PAA levels and neurological adverse events (AEs) was analyzed. Many of the over 30 reports of administration of NaPBA and/or sodium PAA to humans describe AEs, particularly when administered intravenously. IV administration of PAA to cancer patients was shown previously to result in AEs that included fatigue, dizziness, dysgeusia, headache, somnolence, lightheadedness, pedal edema, nausea, vomiting, and rash (Thibault 1994; Thibault 1995). These AEs correlated with PAA levels from 499 to 1285 µg/mL. Although NaPBA has been used in UCD treatment for over two decades and AEs reportedly associated with PAA are similar to those associated with hyperammonemia, little was known previously about the relationship between PAA levels and neurological AEs in UCD patients. As shown herein, increased PAA levels did not correlate with increased neurological AEs in subjects with UCD. However, PAA levels were associated with an increase in neurological AEs in healthy subjects. Based on these results, methods are provided herein for predicting or diagnosing AEs in a subject by measuring PAA levels. Further provided herein are methods of treating and/or preventing AEs in a subject with elevated PAA levels by administering one or more nitrogen scavenging drugs.

Provided herein are specific target values for blood ammonia upon which an effective dosage of a nitrogen scavenging drug can be based. In certain embodiments, an effective dosage of a nitrogen scavenging drug may be an initial dosage, subsequent/maintenance dosage, improved dosage, or a dosage determined in combination with other factors. In certain embodiments, the effective dosage may be the same as or different than the initial dosage. In other embodiments, the effective dosage may be higher or lower than the initial dosage. In certain embodiments, methods are provided for adjusting the dose or regimen of a nitrogen scavenging drug to achieve a target ammonia level that is predictive of the average daily ammonia level and/or the highest ammonia value that the subject is likely to experience during the day.

Using the methods herein, a subject's fasting blood ammonia level may be used as a predictor of daily ammonia burden, average daily ammonia level, and/or highest daily ammonia value. Whether a subject with a nitrogen retention disorder is receiving an optimum dosage of nitrogen scavenging drug may be determined based on predicted daily ammonia exposure. By optimizing the therapeutic efficacy of a nitrogen scavenging drug, the therapeutic dosage of the nitrogen scavenging drug is adjusted so that the subject experiences the desired nitrogen scavenging effect. In particular, the dose is adjusted so that the subject may experience a normal average daily ammonia level. In certain embodiments, the effective dosage of nitrogen scavenging drug is determined by adjusting (e.g., increasing) a dosage to achieve a fasting blood ammonia level for a subject that is less than or equal to half the ULN for blood ammonia.

Provided herein in certain embodiments are methods of determining whether the dosage of a nitrogen scavenging drug needs to be increased in a subject with a nitrogen retention disorder comprising comparing a fasting blood ammonia level for the subject to a ULN for blood ammonia. If the fasting blood ammonia level has a value that greater than half the ULN, the dosage of the nitrogen scavenging drug needs to be increased. In certain embodiments, the methods further comprise increasing the dosage of the nitrogen scavenging drug if the need exists, and in certain of these embodiments the methods further comprise administering the increased dosage. In certain of these embodiments, administration of the increased dosage results in a normal average daily ammonia level in the subject.

Provided herein in certain embodiments are methods of determining whether the dosage of a nitrogen scavenging drug needs to be increased in a subject with a nitrogen retention disorder comprising measuring a fasting blood ammonia level for the subject and comparing the fasting blood ammonia level to a ULN for blood ammonia. If the fasting blood ammonia level has a value that is greater than half the ULN, the dosage of the nitrogen scavenging drug needs to be increased. In certain embodiments, the methods further comprise increasing the dosage of the nitrogen scavenging drug if the need exists, and in certain of these embodiments the methods further comprise administering the increased dosage. In certain of these embodiments, administration of the increased dosage results in a normal average daily ammonia level in the subject.

Provided herein in certain embodiments are methods of adjusting the dosage of a nitrogen scavenging drug in a subject with a nitrogen retention disorder comprising comparing a fasting blood ammonia level for the subject to a ULN for blood ammonia. If the fasting blood ammonia level has a value that is greater than half the ULN, the dosage of the nitrogen scavenging drug is increased, and if the dosage is less than or equal to half the ULN the dosage of the nitrogen scavenging drug is not increased. In certain embodiments, the methods further comprise administering the increased dosage. In certain of these embodiments, administration of the increased dosage results in a normal average daily ammonia level in the subject.

Provided herein in certain embodiments are methods of adjusting the dosage of a nitrogen scavenging drug in a subject with a nitrogen retention disorder comprising measuring a fasting blood ammonia level for the subject and comparing the fasting blood ammonia level to a ULN for blood ammonia. If the fasting blood ammonia level has a value that is greater than half the ULN, the dosage of the nitrogen scavenging drug is increased, and if the dosage is less than or equal to half the ULN the dosage of the nitrogen scavenging drug is not increased. In certain embodiments, the methods further comprise administering the increased dosage. In certain of these embodiments, administration of the increased dosage results in a normal average daily ammonia level in the subject.

Provided herein in certain embodiments are methods of adjusting the dosage of a nitrogen scavenging drug in a subject with a nitrogen retention disorder comprising measuring a fasting blood ammonia level for the subject and comparing the fasting blood ammonia level to a ULN for blood ammonia. If the fasting blood ammonia level has a value that is greater than half the ULN, the dosage of the nitrogen scavenging drug is increased, and if the dosage is significantly less than half the ULN, the dosage of the nitrogen scavenging drug may be decreased. In certain embodiments, the methods further comprise administering the adjusted dosage. In certain of these embodiments, administration of the adjusted dosage results in a normal average daily ammonia level in the subject.

Provided herein in certain embodiments are methods of adjusting the dosage of a nitrogen scavenging drug in a subject with a nitrogen retention disorder comprising administering an initial dosage of the nitrogen scavenging drug, measuring fasting blood ammonia level, and comparing the fasting blood ammonia level to a ULN for blood ammonia. If the fasting blood ammonia level has a value that is greater than half the ULN, subsequent maintenance dosages of the nitrogen scavenging drug are adjusted to be greater than the initial dosage. In certain embodiments, the methods further comprise administering the increased maintenance dosage, and in certain of these embodiments, administration of the increased maintenance dosage results in a normal average daily ammonia level in the subject.

Provided herein in certain embodiments are methods of adjusting the dosage of a nitrogen scavenging drug in a subject with a nitrogen retention disorder to achieve a fasting blood ammonia level that is less than or equal to half the ULN for blood ammonia comprising measuring a fasting blood ammonia level for the subject and comparing the fasting blood ammonia level to a ULN for blood ammonia. If the fasting blood ammonia level has a value that is greater than half the ULN, the subject is administered an increased dosage of the nitrogen scavenging drug. After a time period sufficient for the drug to reach steady state (e.g., 48 hours, 48 to 72 hours, 72 hours to 1 week, 1 week to 2 weeks, greater than 2 weeks), fasting blood ammonia level is measured again and compared to a ULN for blood ammonia. If the fasting blood ammonia level has a value that is greater than half the ULN, the dosage of the nitrogen scavenging drug is increased. This process is repeated until a fasting blood ammonia level of less than or equal to half the ULN is obtained.

Provided herein in certain embodiments are methods for assessing whether a subject with a nitrogen retention disorder is more or less likely to need a dosage adjustment of a nitrogen scavenging drug comprising measuring a fasting blood ammonia level for the subject and comparing the fasting blood ammonia level to a ULN for blood ammonia, wherein a fasting blood ammonia level that is greater than half the value of ULN indicates that the subject is more likely to need a dosage adjustment and a fasting blood ammonia level less than or equal to half the value of ULN indicates that the subject is less likely to need a dosage adjustment.

Provided herein in certain embodiments are methods of determining whether to administer a nitrogen scavenging drug to a subject with nitrogen retention disorder comprising comparing a fasting blood ammonia level for the subject to a ULN for blood ammonia. If the fasting blood ammonia level has a value that is greater than half the ULN, a nitrogen scavenging drug needs to be administered to the subject. In certain embodiments, these methods further comprise administering the nitrogen scavenging drug. In certain embodiments, the subject may not have been administered any nitrogen scavenging drugs prior to the determination. In other embodiments, the subject may have previously been administered a nitrogen scavenging drug other than the one being evaluated. In these embodiments, the methods provided herein can be used to determine whether to administer a new nitrogen scavenging drug to a subject.

Provided herein in certain embodiments are methods of determining whether to administer a nitrogen scavenging drug to a subject with nitrogen retention disorder comprising measuring a fasting blood ammonia level for the subject and comparing the fasting blood ammonia level to a ULN for blood ammonia. If the fasting blood ammonia level has a value that is greater than half the ULN, a nitrogen scavenging drug needs to be administered to the subject. In certain embodiments, these methods further comprise administering the nitrogen scavenging drug. In certain embodiments, the subject may not have been administered any nitrogen scavenging drugs prior to the determination. In other embodiments, the subject may have previously been administered a nitrogen scavenging drug other than the one being evaluated. In these embodiments, the methods provided herein can be used to determine whether to administer a new nitrogen scavenging drug to a subject.

Provided herein in certain embodiments are methods for selecting a dosage of a nitrogen scavenging drug for treating a nitrogen retention disorder in a subject based on blood ammonia levels comprising selecting a dosage that results in a fasting blood ammonia level that is less than or equal to half the ULN for blood ammonia. In certain embodiments, selecting the effective dosage is further based on diet, endogenous waste nitrogen excretion capacity, or any combination thereof. In certain embodiments, the methods further comprise administering the selected dosage.

Provided herein in certain embodiments are methods of treating a subject with a nitrogen retention disorder who has previously been administered a nitrogen scavenging drug comprising measuring a fasting blood ammonia level for the subject and comparing the fasting blood ammonia level to a ULN for blood ammonia. If the fasting blood ammonia level has a value that is greater than half the ULN, the subject is administered an increased dosage of the nitrogen scavenging drug. If the fasting blood ammonia level has a value that is less than or equal to half the ULN, the subject is administered the same dosage or a decreased dosage of the nitrogen scavenging drug. In certain embodiments, administration of an increased dosage results in a normal average daily ammonia level in the subject.

Provided herein in certain embodiments are methods of treating a subject with a nitrogen retention disorder who has previously been administered an initial dosage of a nitrogen scavenging drug comprising measuring a fasting blood ammonia level for the subject and comparing the fasting blood ammonia level to a ULN for blood ammonia. If the fasting blood ammonia level has a value that is greater than half the ULN, the subject is administered a maintenance dosage that is greater than the initial dosage of the nitrogen scavenging drug. If the fasting blood ammonia level has a value that is less than or equal to half the ULN, the subject is administered the initial dosage or a lower dosage. In certain embodiments, administration of an increased maintenance dosage results in a normal average daily ammonia level in the subject.

Provided herein in certain embodiments are methods of treating a subject with a nitrogen retention disorder comprising administering a nitrogen scavenging drug, then measuring a fasting blood ammonia level for the subject at some point after drug administration and comparing the fasting blood ammonia level to a ULN for blood ammonia. If the fasting blood ammonia level has a value that is greater than half the ULN, the subject is administered an increased dosage of the nitrogen scavenging drug. If the fasting blood ammonia level has a value that is less than or equal to half the ULN, the subject is administered the original or a lower dosage of the drug.

Provided herein in certain embodiments are methods of treating a subject with a nitrogen retention disorder comprising administering a first dosage of a nitrogen scavenging drug, measuring a fasting blood ammonia level for the subject, and comparing the fasting blood ammonia level to a ULN for blood ammonia. If the fasting blood ammonia level has a value that is greater than half the ULN, a second dosage of a nitrogen scavenging drug that is greater than the first dosage is administered to the subject. A fasting ammonia blood level is measured again in the subject and compared to a ULN for blood ammonia. If the fasting blood ammonia level has a value that is greater than half the ULN, a third dosage of a nitrogen scavenging drug that is greater than the second dosage is administered to the subject. This process is repeated until the subject exhibits a fasting blood ammonia level with a value less than or equal to half the ULN.

Provided herein in certain embodiments are methods of monitoring the efficacy of nitrogen scavenging drug administration in a subject with a nitrogen retention disorder who has previously been administered a nitrogen scavenging drug comprising measuring a fasting blood ammonia level for the subject and comparing the fasting blood ammonia level to a ULN for blood ammonia. If the fasting blood ammonia level has a value that is greater than half the ULN, the previously administered dosage of the nitrogen scavenging drug is considered inadequate to treat the nitrogen retention disorder. If the fasting blood ammonia level has a value that is less than or equal to half the ULN, the previously administered dosage is considered adequate to treat the nitrogen retention disorder. In certain embodiments where the previously administered dosage is considered inadequate to treat the nitrogen retention disorder, the methods provided herein further comprise administering an increased dosage of the nitrogen scavenging drug.

Provided herein in certain embodiments are methods for monitoring therapy with a nitrogen scavenging drug in a subject having a nitrogen retention disorder comprising measuring a fasting blood ammonia level from the subject and comparing the fasting blood ammonia level to a ULN for blood ammonia, wherein a fasting blood ammonia level that is greater than half the ULN indicates that the subject is more likely to need a dosage adjustment of the nitrogen scavenging drug, and wherein a fasting blood ammonia level less than or equal to half the ULN indicates that the subject is less likely to need a dosage adjustment.

A nitrogen retention disorder as used herein refers to any condition associated with elevated blood nitrogen/ammonia levels. In certain embodiments, a nitrogen retention disorder may be a UCD. In other embodiments, a nitrogen retention disorder may be HE.

A nitrogen scavenging drug as used herein refers to any drug that decreases blood nitrogen and/or ammonia levels. In certain embodiments, a nitrogen scavenging drug may remove nitrogen in the form of PAGN, and in certain of these embodiments the nitrogen scavenging drug may be an orally administrable drug that contains or is metabolized to PAA. For example, a nitrogen scavenging drug may be a PAA prodrug such as PBA or HPN-100, a pharmaceutically acceptable salt of PBA such as NaPBA, or a pharmaceutically acceptable ester, acid, or derivative of a PAA prodrug. In other embodiments, a nitrogen scavenging drug may remove nitrogen via hippuric acid. In certain of these embodiments, a nitrogen scavenging drug may be benzoic acid, a pharmaceutically acceptable salt of benzoic acid such as sodium benzoate, or a pharmaceutically acceptable ester, acid, or derivative of benzoic acid.

Increasing the dosage of a nitrogen scavenging drug may refer to increasing the amount of drug per administration (e.g., an increase from a 3 mL dosage to a 6 mL dosage), increasing the number of administrations of the drug (e.g., an increase from once-a-day dosing to twice- or three-times-a-day), or any combination thereof.

A subject that has previously been administered a nitrogen scavenging drug may have been administered the drug for any duration of time sufficient to reach steady state. For example, the subject may have been administered the drug over a period of 2 to 7 days, 1 week to 2 weeks, 2 weeks to 4 weeks, 4 weeks to 8 weeks, 8 weeks to 16 weeks, or longer than 16 weeks.

In certain embodiments of the methods disclosed herein, the fasting period for obtaining a fasting blood ammonia level is overnight. In certain embodiments, the fasting period is 4 hours or more, 5 hours or more, 6 hours or more, 7 hours or more, 8 hours or more, 9 hours or more, 10 hours or more, 11 hours or more, or 12 hours or more, and in certain embodiments the fasting period is 4-8 hours, 6-8 hours, or 8-12 hours. During the fasting period, the subject preferably does not ingest any food. In certain embodiments, the subject may also refrain from ingesting certain non-food substances during the fasting period. For example, in certain embodiments the subject does not ingest any supplements and/or nitrogen scavenging drugs during the fasting period. In certain of these embodiments, the subject may nonetheless ingest one or more drugs other than nitrogen scavenging drugs during the fasting period. In certain embodiments, the subject does not ingest any high calorie liquids during the fasting period. In certain of these embodiments, the subject does not ingest any liquids other than water during the fasting period. In other embodiments, the subject may ingest small amounts of low calorie beverages, such as tea, coffee, or diluted juices.

In certain embodiments of the methods disclosed herein, blood samples used for measuring fasting blood ammonia levels and/or ULN blood ammonias are venous blood samples. In certain embodiments, a blood sample is a plasma blood sample. Any methods known in the art may be used to obtain a plasma blood sample. For example, blood from a subject may be drawn into a tube containing heparin or ethylenediaminetetraacetic acid (EDTA). In certain embodiments, the sample can be placed on ice and centrifuged to obtain plasma within 15 minutes of collection, stored at 2-8° C. (36-46° F.) and analyzed within 3 hours of collection. In other embodiments, the blood plasma sample is snap frozen, stored at ≤−18° C. (≤0° F.) and analyzed at a later time. For example, the sample may be analyzed at 0-12 hours, 12-24 hours, 24-48, 48-96 hours after freezing, or within any other timeframe over which the sample has demonstrated stability. In certain embodiments, blood samples are taken in a laboratory or hospital setting. In certain embodiments, a single fasting blood sample is used to measure fasting blood ammonia level. However, in other embodiments, multiple fasting blood samples may be obtained. In certain embodiments, a subject's blood ammonia level may be monitored throughout the day. Further, in certain embodiments, the methods disclosed herein comprise an additional step of obtaining one or more blood samples from a subject prior to or after measuring fasting blood ammonia level.

In certain embodiments, a blood sample is analyzed immediately after collection. In other embodiments, the blood sample is stored for some period between collection and analysis. In these embodiments, the sample may be stored for less than 1 hour, 1 hour to 6 hours, 1 hour to 12 hours, 1 hour to 24 hours, or 1 hour to 48 hours. In certain of these embodiments, the blood sample is stored at a temperature between 0-15° C., such as 2-8° C. In other embodiments, the blood sample is stored below 0° C. or below −18° C.

Measurement of ammonia levels in a fasting blood sample is carried out using techniques known in the art. For example, ammonia levels may be measured using a colorimetric reaction or an enzymatic reaction. In certain embodiments, a colorimetric reaction may involve the use of bromophenol blue as an ammonia indicator. In these embodiments, ammonia may react with bromophenol blue to yield a blue dye. In certain embodiments, an enzymatic reaction may involve glutamate dehydrogenase catalyzing the reductive amination of 2-oxoglutarate with $NH^{4+}$ and NADPH to form glutamate and $NADP^+$. The formation of $NADP^+$ formed is directly proportional to the amount of ammonia present in the blood sample. Therefore, the concentration of ammonia is measured based on a decrease in absorbance.

In certain embodiments of the methods disclosed herein, a subject exhibiting a fasting blood ammonia level less than or equal to half the ULN for blood ammonia has an average likelihood within a confidence interval that their average daily ammonia level will remain within a normal average daily ammonia level. In certain embodiments, the average likelihood of having a normal daily ammonia value is 80% to 90%. In certain embodiments, one may predict with 95% confidence that a blood ammonia level will fall within a certain range. In certain embodiments, one can predict with 95% confidence that a true probability of predicting normal values based on fasting blood ammonia is between 65% and 93%. In other embodiments, one can predict with 80% confidence that a true probability of predicting normal values based on fasting blood ammonia is at least 70%. In certain embodiments, the average likelihood of predicting normal ammonia value based on fasting blood ammonia is about 84% with 95% confidence that the true probability is between 65% and 93%.

In certain embodiments of the methods disclosed herein, a subject exhibiting a fasting blood ammonia level less than or equal to half the ULN for blood ammonia has an average likelihood within a confidence interval that their maximum daily blood ammonia level will not exceed 1.5 times the ULN for blood ammonia. In certain of these embodiments, the average likelihood is about 70% to 80%. In certain embodiments, the confidence interval is a 95% confidence interval. In certain embodiments, the average likelihood is about 75% with 95% confidence that the true probability is between 58% and 86%.

In certain embodiments of the methods disclosed herein, a subject exhibiting a fasting blood ammonia level less than or equal to half the ULN for blood ammonia has an average likelihood within a confidence interval that their maximum daily blood ammonia level will be less than 100 µmol/L. In certain of these embodiments, the average likelihood is 90% to 98%. In certain embodiments, the confidence interval is 95%. In certain embodiments, the average likelihood is about 93% with 95% confidence that the true probability is between 77% and 100%.

The maximal ammonia value refers to the maximum amount of ammonia that may be detected in a subject following consumption of meals, if repeated measurement of blood ammonia can be instituted to detect such maximum value over an extended period of time. Based on well-controlled clinical trials with repeated blood sampling over 24 hours, the maximum blood ammonia has been observed to occur following the third major meal of the day in the early to mid evening hours (4-8 PM, assuming that breakfast is approximately 8 AM; see, e.g., Lee 2010; Lichter-Konecki 2011).

The ULN for blood ammonia typically represents the highest level in the range of normal values, which may be influenced by a variety of factors such as the assay method, types of regents, standard reference samples used, and specifications and calibration of equipment used to perform the measurement. In certain embodiments of the methods disclosed herein, the ULN for blood ammonia is determined for a subject individually. In other embodiments, the ULN for blood ammonia may be based on measurements obtained across a range of subjects (i.e., subjects with UCD or with a particular subtype of UCD, subjects with HE, healthy subjects, etc.). In certain embodiments, the ULN for blood ammonia may represent a standard reference value disclosed in the art, such as a mean ULN developed across a particular subset of subjects. In other embodiments, the ULN for blood ammonia may represent a standard measurement that has been developed by a particular entity that performs blood draws and/or blood evaluations, such as a particular clinical laboratory. In certain embodiments, the ULN is a standard reference value utilized by the same entity that measures the fasting blood ammonia level. In these embodiments, one skilled in the art will appreciate that interpretation of average daily ammonia in subject with a nitrogen retention disorder must be made relative to the reference range of normal values at the laboratory in which the ammonia was measured. Furthermore, the units of ammonia measurement may also vary from lab to lab (e.g., µg/mL or µmol/L), emphasizing the importance of interpreting the subject's ammonia levels relative to the ULN at the laboratory in which the measurement was performed. In certain embodiments, the ULN for blood ammonia may be in the range of 26-64 µmol/L. In certain of these embodiments, the ULN for blood ammonia may be in the range of 32-38 µmol/L or 34-36 µmol/L, and in certain of these embodiments the ULN for blood ammonia is 35 µmol/L. In certain embodiments, the ULN for blood ammonia may be in the range of 50-65 µg/mL. In certain of these embodiments, the ULN for blood ammonia may be in the range of 55-63 µg/mL or 57-61 µg/mL, and in certain of these embodiments the ULN for blood ammonia is 59 µg/mL.

In certain embodiments, the average daily ammonia is the average amount of ammonia an individual may experience during the day, if serial blood sampling were performed for ammonia measurements. In well-controlled clinical studies, it has been established that ammonia fluctuates several fold during the day, depending on the timing of blood draw relative to food and drug intake. Due to these fluctuations, the timing of individual or serial blood sampling should be controlled relative to the timing of food and drug intake. Even serial sampling may not be enough to capture the peaks and troughs of the fluctuating ammonia values, unless samples are taken frequently enough. Therefore, obtaining a simple average of several measurements may provide inadequate or misleading information regarding the total ammonia burden a subject may experience during the day.

Provided herein are methods to better estimate a subject's average daily ammonia assessed as the area under the curve for 24-hr ammonia (ammonia $AUC_{0-24\ hr}$) obtained from adequate and well-spaced samples over 24 hours. This ammonia $AUC_{0-24\ hr}$ can be further normalized for the entire actual period of sampling, i.e., ammonia $AUC_{0-24\ hr}$ is divided by the sampling period (e.g., 24 hours). For example, if an AUC of 1440 µmol*hr/L is calculated using the trapezoidal rule based on 8-11 ammonia values obtained over 24 hours, then the average daily ammonia value or time-normalized $AUC_{0-24\ hr}$ would be equal to 1440 µmol*hr/ml divided by the sampling time of 24 hr, or 60 µmol/L. If the normal reference range at the laboratory which performed the ammonia analysis was 10-35 µmol/L, then the average daily ammonia value for this subject would be approximately 1.71 times the ULN of 35 µmol/L. Similarly, if the ammonia $AUC_{0-24\ hr}$ was determined to be equal to 840 µmol*hr/L based on multiple, well-spaced samples over 24 hours and analyzed at the same laboratory, and the sampling period was 24 hours, then the time-normalized $AUC_{0-24\ hr}$ would be 35 µmol/L. This corresponds to an average ammonia or daily ammonia burden within the ULN. Finally, subjects with nitrogen retention disorders such as UCDs may experience a hyperammonemic crisis, which is often defined clinically as a blood level exceeding 100 µmol/L and clinical manifestations of hyperammonemia, which may require intervention to prevent irreversible hard and enable recovery.

Provided herein are methods of adjusting nitrogen scavenging drug dosage by measuring fasting blood ammonia to minimize the likelihood a subject may experience an ammonia value (Cmax) over 24 hours that exceeds 100 µmol/L. It has been found that 100 µmol/L corresponds to approximately 2-3 times the ULN in most laboratories. Previously, if a subject with a nitrogen retention disorder such as UCD had a blood ammonia level within or slightly above the normal reference range for the laboratory which performed the analysis, the subject was considered to be in good clinical control regardless of the timing of the blood draw in relation to meals and last administration of drug dose. However, it has been shown that a subject with a UCD who has a fasting blood ammonia level between the ULN and 1.5 times the ULN (e.g., 35 to 52 µmol/L) has an average likelihood of only 45% (with a 95% confidence interval of 21% to 70%) that his or her average daily ammonia is within the normal range; an average likelihood of only 35% (with a 95% confidence interval of 13% to 60%) that his or her maximal level of ammonia during the day is less than 1.5 times the ULN (e.g., 52 µmol/L); and an average likelihood of 25% that his or her maximal daily ammonia level exceeds 100 µmol/L during the day. Thus, after measuring a UCD subject's fasting blood ammonia, the dosage of a nitrogen scavenging drug may be progressively increased and/or his or her protein intake progressively decreased until the fasting ammonia value is less than or equal to half of the ULN for the local laboratory in which the ammonia analysis was performed.

In certain embodiments of the methods disclosed herein, one or more factors other than ammonia level may be taken into consideration when evaluating nitrogen scavenging drug dosage. For example, blood ammonia measurements may be combined with urinary PAGN measurements in determining whether to administer a nitrogen scavenging drug, adjusting the dosage of a nitrogen scavenging drug, or treating a nitrogen retention disorder. US Patent Publication No. 2010/0008859 discloses that urinary PAGN levels correlate more closely to PBA prodrug dosage than plasma PAA, PBA, or PAGN levels, and further discloses that PBA prodrugs are converted to urinary PAGN with a mean efficiency of 60-75%. Therefore, certain embodiments of the methods disclosed herein comprise an additional step wherein urinary PAGN levels are measured. In certain of these embodiments, calculation of an effective dosage of nitrogen scavenging drug is based in part on a mean 60-75% conversion of PAA prodrug to urinary PAGN. For example, in certain embodiments the methods disclosed herein for determining whether to administer a nitrogen scavenging drug to a subject comprise an additional step of measuring urinary PAGN and calculating an effective initial dosage based on a mean conversion of PAA prodrug to urinary PAGN of 60-75%. Similarly, in certain embodiments the methods disclosed herein for adjusting the dosage of a nitrogen scavenging drug comprise an additional step of measuring urinary PAGN and calculating an effective dosage based on a mean conversion of PAA prodrug to urinary PAGN of 60-75%. In certain of these embodiments, the effective dosage is calculated based on a target nitrogen output. In certain embodiments, urinary PAGN may be determined as a ratio of the concentration of urinary PAGN to urinary creatinine. In certain embodiments, urinary PAGN is a factor that is taken into consideration when determining whether to administer or increase the dosage of a nitrogen scavenging drug, i.e., urinary PAGN is evaluated in combination with ammonia level to determine whether to administer or increase the dosage of the drug. In other embodiments, ammonia level alone is used to determine whether to administer or increase the dosage of a nitrogen scavenging drug, and urinary PAGN is simply used to calculate the initial or adjusted dosage.

One skilled in the art will recognize that a variety of other factors may be taken into consideration when determining the effective dosage of a nitrogen scavenging drug. For example, factors such as diet (e.g., protein intake) and endogenous waste nitrogen capacity (e.g., urea synthesis capacity) may be considered.

Provided herein in certain embodiments are kits for carrying out the methods disclosed herein. In certain embodiments, kits are provided for determining whether to administer or adjust the dosage of a nitrogen scavenging drug for a subject with a nitrogen retention disorder. The kits disclosed herein may include one or more nitrogen scavenging drugs and/or one or more reagents (e.g., bromophenol blue) or enzymes (e.g., glutamate dehydrogenase) to measure blood ammonia levels in a sample. The kit may additionally include other pigments, binders, surfactants, buffers, stabilizers, and/or chemicals necessary to obtain a blood sample and to measure the ammonia level in the sample. In certain embodiments, the kits provided herein comprise instructions in a tangible medium.

One of ordinary skill in the art will recognize that the various embodiments described herein can be combined.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Figure 3A:
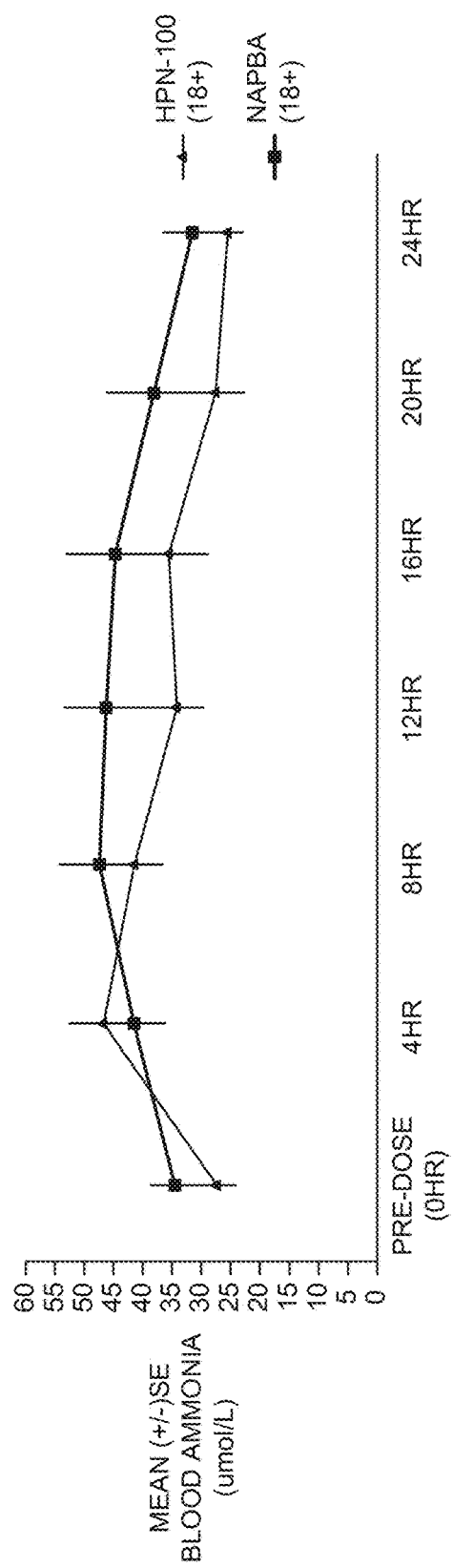
FIG. 3: Venous blood ammonia values over 24 hours in (A) adult and (B) pediatric UCD patients.
Figure 3B:
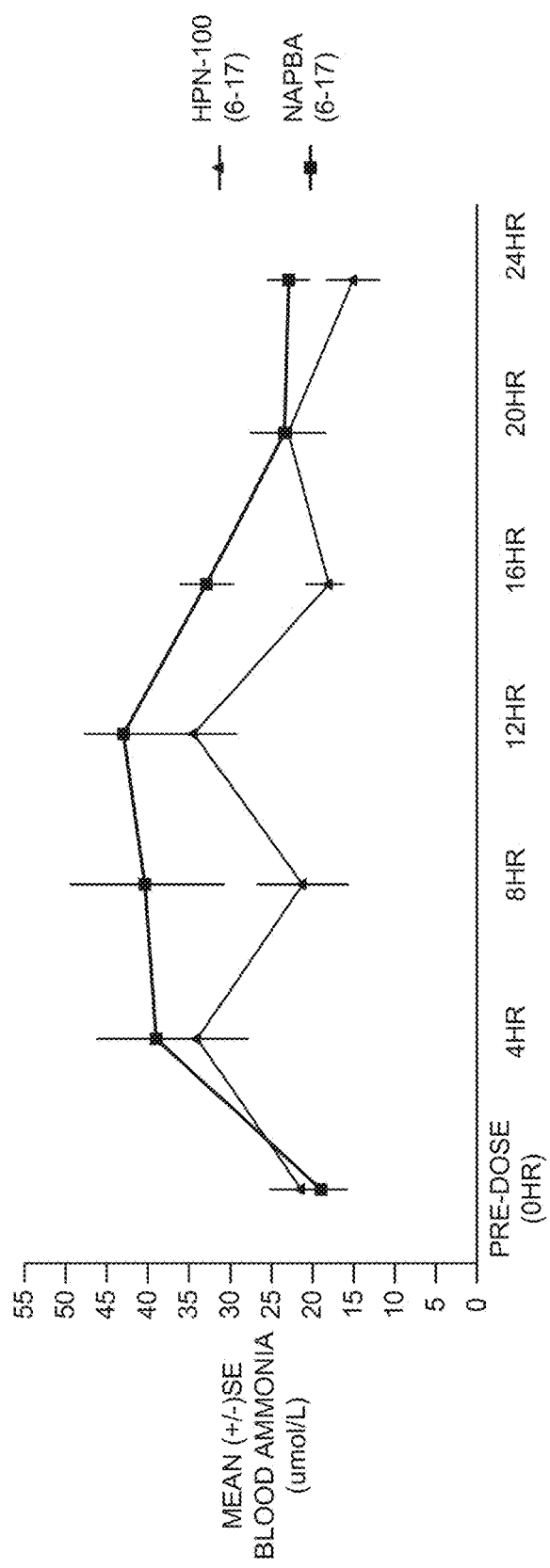

Example 1: Analysis of Predictability of Pharmacodynamic Ammonia Values from Fasting Ammonia in UCD Patients This example demonstrates the relationship between fasting ammonia and the pharmacodynamic (PD) profile of daily ammonia in patients receiving PAA prodrugs for UCDs. Ammonia values vary many-fold over the course of 24 hours in UCD patients. As depicted in FIGS. 3a and 3b, venous ammonia was measured for 24 hours following one week of dosing with either NaPBA or glycerol phenylbutyrate (GPB). The graphs display ammonia values as mean±SD over 24 hours, where time zero corresponds to just prior to dosing and breakfast (i.e., fasting state). In view of this variability in daily ammonia levels, a single measurement may not be very informative in determining whether a UCD patient is optimally dosed. The ability to predict the highest potential ammonia a UCD patient may experience during the day and the average 24-hour ammonia from a single measurement such as fasting levels has important practical implications for nitrogen scavenging drug dosing guidelines and patient management.

Data from two Phase 2 studies and one Phase 3 study comparing ammonia control assessed by 24-hour sampling during steady state treatment with HPN-100 versus NaPBA in 65 UCD patients were used for the analysis. The two Phase 2 studies include protocols UP 1204-003 and HPN-100-005 (Lee 2010; Lichter-Konecki 2011). The Phase 3 study includes protocols from HPN-100-006 (Diaz 2011).

Ammonia values obtained from different hospital laboratories with different normal ranges were normalized to a standard laboratory range of 9-35 µmol/L. The patient population included a broad range of ages, UCD subtypes, and doses of drug, and is summarized in Table 1 below.

TABLE 1

UCD demographics in studies UP 1204-003, HPN-100-005, and HPN-100-006:

| Gender | Male | 18 (27.7) |
|---|---|---|
| n (%) | Female | 47 (72.3) |
| Age at screening | N | 65 |
| (years) | Mean (SD) | 29.46 (15.764) |
| | Median | 24.00 |
| | Range | 6.0-75.0 |

TABLE 1-continued

UCD demographics in studies UP 1204-003, HPN-100-005, and HPN-100-006:

| UCD diagnosis | OTC deficiency | 57 (87.7) |
|---|---|---|
| n (%) | CPS1 deficiency | 1 (1.5) |
| | ASS deficiency | 5 (7.7) |
| | ASL deficiency | 1 (1.5) |
| | Missing | 1 (1.5) |
| Duration of NaPBA | N | 63 |
| treatment | Mean (SD) | 114.14 (90.147) |
| (months) | Median | 101.00 |
| | Range | 0.2-300.0 |
| Daily dose NaPBA | N | 64 |
| | Mean (SD) | 14.10 (6.255) |
| | Median | 13.50 |
| | Range | 1.5-36.0 |

Exploratory Analysis:

Several PD parameters for steady-state ammonia were explored: $AUC_{0-24\,hr}$, time-normalized AUC, log AUC, maximal ammonia value over 24 hours (Cmax), and average ammonia. Data from 65 subjects from all three studies with steady-state ammonia and fasting ammonia were used. Missing data were imputed per procedures specified in the protocol and statistical analysis plan, except that no imputations were made for subjects who had no PK sampling conducted while on a given study drug.

Sample collection times of 0-hr (before first daily dose) and 24-hours post-dose (before first daily dose of the following day) were both evaluated as representative of fasting ammonia. No noticeable difference in the shape or quality of the relationship due to the choice of time point was observed.

The relationship between fasting ammonia and pharmacokinetic profile was evaluated separately for HPN-100 and NaPBA, with no apparent difference in the strength or magnitude of the relationship. Therefore, all data from both HPN-100 and NaPBA treatments were used and conclusions regarding fasting ammonia pertain to both HPN-100 and NaPBA.

Figure 2:
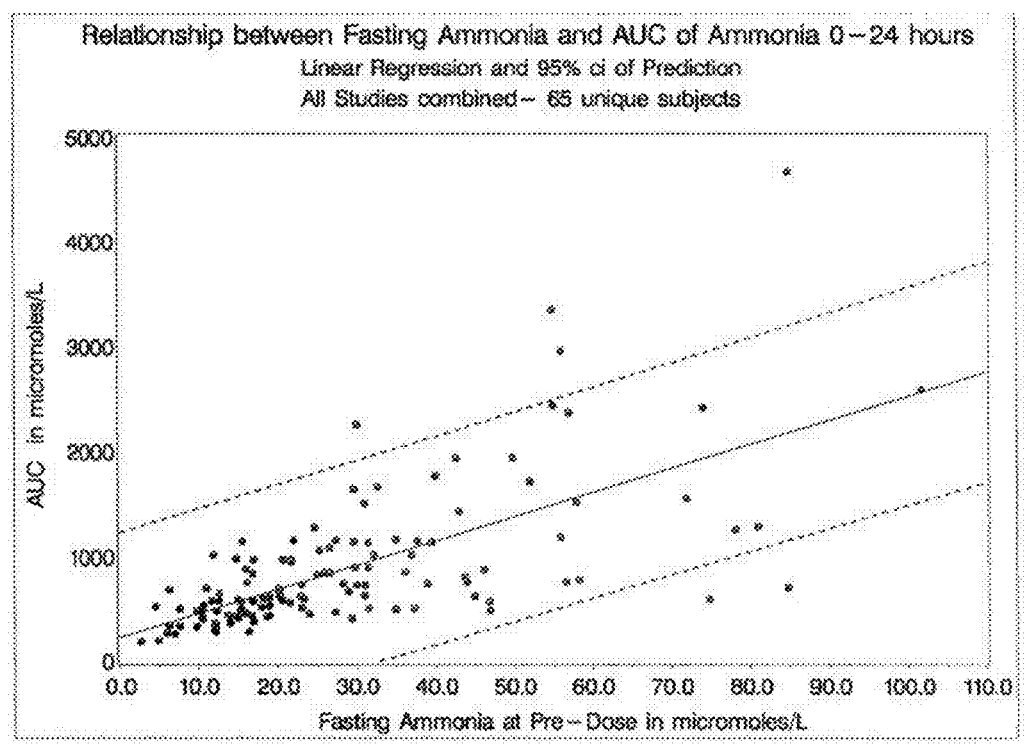
FIG. 2: Relationship between fasting ammonia and average ammonia UCD patients.

The relationships between (1) fasting ammonia and $AUC_{0-24\,hr}$ and (2) fasting ammonia and maximum observed ammonia (Cmax) were visually explored for the whole population. The effects of the following covariates were also observed: age, weight, gender, and dietary protein intake. A positive and strong relationship was observed between fasting ammonia and $AUC_{0-24\,hr}$, with increasing fasting ammonia being associated with higher $AUC_{0-24\,hr}$ and maximum observed ammonia (FIG. 2).

Prediction of $AUC_{0-24\,hr}$ Through GEE Modeling:

The aim of this modeling was to predict average daily or highest achieved ammonia based on the subject's fasting ammonia. In order to take into account the differences in normal ranges at different laboratories, all ammonia values were normalized to a reference range of 9-35 µmol/L, and the predictions were referenced to the ULN rather than a fixed value.

Generalized Estimating Equations (GEE) were used to model the predictive ability of fasting ammonia against various ammonia PD properties. GEE methodology can be used to analyze repeated measures of categorical data, in which the repeated measures are assumed to be correlated (Liang 1986). The model allows for the specification of the assumed correlation structure without the knowledge of the magnitude of the correlation.

The 24-hour ammonia profile was divided into ordered categories using a variety of endpoints and cutpoints as follows:
1) AUC [0-1.0*ULN, >1.0*ULN];
2) AUC [0-1.5*ULN, >1.5*ULN];
3) Cmax [0-1.0*ULN, >1.0*ULN];
4) Cmax [0-1.5*ULN, >1.5*ULN]; and
5) Cmax [0-100] mol/L.

Three levels of fasting ammonia were considered in separate models as input:
1) [0-0.5*ULN];
2) [>0.5*ULN-<1.0 ULN]; and
3) [>1.0*ULN-1.5*ULN].

Using Statistical Analysis Software (SAS) Proc Genmod, generalized linear models were fit with a logit link function. Pre-dose fasting ammonia was the only predictor variable in the model. The repeated nature of the data (two study periods per subject) was modeled using GEE with exchangeable correlation matrix. ULN for fasting ammonia was set at 35 μmol/L. ULN for AUC over 24 hours was taken as 840 (35 mol/L*24 hours); i.e., the AUC which corresponds to an average daily ammonia less than or equal to 35 μmol/L, which was the normalized ULN among the participating study sites and is derived by dividing the 24-hour area under the curve by the sampling time of 24 hours. The GEE model was bootstrap-resampled 1,000 times according to the method outlined in Davison, A. C. & Hinkley, D. V., Bootstrap Methods and their Application, Cambridge University Press, London (1997), pp. 358-362. The results of these models are shown in Table 2 below.

TABLE 2

Summary of results from GEE model to predict ability of fasting ammonia against various ammonia PD properties:

| Model # | Fasting ammonia level | Ammonia PK outcome | Probability of outcome in category | Bootstrap 95% c.i. | Bootstrap 80% c.i. | Bootstrap pred. error rate* (%) |
|---|---|---|---|---|---|---|
| 1 | [0-0.5 ULN] | AUC in 24 hours [0-1.0 ULN] | 0.84 | 0.67, 0.93 | 0.71, 0.89 | 11.5 |
| 2 | | AUC in 24 hours [0-1.5 ULN] | | Did not converge | | |
| 3 | | Cmax observed [0-1.0 ULN] | 0.53 | 0.38, 0.65 | 0.42, 0.61 | 45.8 |
| 4 | | Cmax observed [0-1.5 ULN] | 0.76 | 0.61, 0.86 | 0.66, 0.82 | 23.3 |
| 5 | | Cmax observed [0-100] | 0.93 | 0.78, 1.00 | 0.85, 0.97 | 5.7 |
| 6 | [0-<1.0 ULN] | AUC in 24 hours [0-1.0 ULN] | 0.58 | 0.42, 0.73 | 0.48, 0.68 | 42.8 |
| 7 | | AUC in 24 hours [0-1.5 ULN] | 0.88 | 0.78, 0.97 | 0.82, 0.94 | 11.1 |
| 8 | | AUC in 24 hours [0-2 ULN] | 0.97 | 0.90, 1.00 | 0.93, 1.00 | 2.2 |
| 9 | | Cmax observed [0-1.0 ULN] | 0.21 | 0.11, 0.38 | 0.14, 0.33 | 20.0 |
| 10 | | Cmax observed [0-1.5 ULN] | 0.52 | 0.35, 0.66 | 0.42, 0.61 | 46.0 |
| 11 | | Cmax observed [0-2.0 ULN] | 0.74 | 0.62, 0.85 | 0.91, 1.00 | 27.2 |
| 12 | | Cmax observed [0-100] | 0.95 | 0.88, 1.00 | 0.66, 0.81 | 4.3 |
| 13 | [>1.0-1.5 ULN] | AUC in 24 hours [0-1.0 ULN] | 0.45 | 0.24, 0.71 | 0.30, 0.63 | 43 |
| 14 | | AUC in 24 hours [0-1.5 ULN] | | Did not converge | | |
| 15 | | AUC in 24 hours [0-2 ULN] | 0.80 | 0.49, 0.99 | 0.63, 0.92 | 27 |
| 16 | | Cmax observed [0-1.0 ULN] | | Did not converge | | |
| 17 | | Cmax observed [0-1.5 ULN] | 0.35 | 0.16, 0.58 | 0.23, 0.51 | 33 |

TABLE 2-continued

Summary of results from GEE model to predict ability of
fasting ammonia against various ammonia PD properties:

| Model # | Fasting ammonia level | Ammonia PK outcome | Probability of outcome in category | Bootstrap 95% c.i. | Bootstrap 80% c.i. | Bootstrap pred. error rate* (%) |
|---|---|---|---|---|---|---|
| 18 | | Cmax observed [0-2.0 ULN] | Did not converge | | | |
| 19 | | Cmax observed [0-100] | Did not converge | | | |

From Table 2 above, we can conclude that in the population of UCD patients described in Table 1, we can be 95% confident that, given a fasting ammonia less than or equal to half the ULN, the true probability of having an AUC in the range [0-840] is on average 84%, at least 67%, and as high as 93%.

Row 1 of Table 2 above suggests that a UCD patient with a fasting ammonia of 17 μmol/L as determined by a laboratory with a normal reference range of 9-35 μmol/L (i.e., a fasting ammonia in the range [0-0.5 ULN]) has an 84% chance (with a 95% confidence interval of 67% to 93%) of having a time normalized $AUC_{0-24\ hr}$ in the normal range [$AUC_{0-24\ hr}$ of 0-840 or an average daily ammonia of 35 μmol/L], a 76% chance (with a 95% confidence interval of 61% to 86%) of having a Cmax of less than 1.5 ULN, and a 93% chance (with a 95% confidence interval of 78% to 100%) of never having an ammonia of more than 100 μmol/L. Therefore, this patient would be optimally controlled and unlikely to suffer from high ammonia during the day.

This Example shows that fasting ammonia correlates strongly with daily ammonia exposure, assessed as a daily average or as maximal daily concentration, and that a target fasting value which does not exceed half of the upper level of normal for the local lab appears to be a clinically useful as well as practical predictor of ammonia values over 24 hours as well. Furthermore, this Example shows that a subject with a fasting ammonia in the range 0-0.5 ULN has an 84% chance of having an $AUC_{0-24\ hr}$ in the normal range (0-840 or an average daily ammonia of 35 μmol/L).

Example 2: Selecting and Adjusting HPN-100 Dosage Based on Fasting Blood Ammonia Levels in a Patient with UCD Patient A is an adult with UCD being managed with amino acid supplements and dietary protein restriction only. Patient A consumes neither his supplements nor food for approximately 8 hours prior to a fasting morning blood draw. A venous blood draw is performed, and fasting blood ammonia level is determined to be 52 μmol/L. This fasting blood ammonia level is compared to the ULN for blood ammonia in the laboratory performing the blood draw, which is 35 μmol/L. Based on the correlation of fasting ammonia level to average ammonia level, it is determined that Patient A's fasting blood ammonia level of approximately 1.5 times the ULN represents only a 45% chance on average of having an average ammonia during the day within the normal range. Thus, the ratio of fasting blood ammonia level to ULN for blood ammonia indicates that Patient A will benefit from treatment with a nitrogen scavenging drug.

The physician elects to treat Patient A with HPN-100. Initial dosage is determined based on body surface area or as otherwise instructed according to HPN-100 drug labeling. Patient A's body surface area is 1.4 m², and therefore the initial dosage is determined to be 9 mL per day or 3 mL TID, which is approximately 60% of the maximum allowed dosage per HPN-100 label. Patient A is treated with 9 mL/day of HPN-100 for at least 7 days, and returns for an additional blood draw. The fasting blood ammonia level at this time is 33 μmol/L, which is slightly below the ULN and falls into the range of 0.5 to 1.0 times normal. Patient A's blood ammonia level is monitored throughout the day after administration of a 3 mL dose of HPN-100 with each meal. It is observed that Patient A's maximum ammonia reaches 95 μmol/L after dinner with an average daily ammonia of 66 mol/L, which is almost two times the upper normal range. Therefore, Patient A's dosage of HPN-100 is increased by approximately one-third to 12 mL total or 4 mL TID. Patient A returns after at least 7 days of treatment with HPN-100. Patient A's fasting ammonia level is 15 mol/L, which is less than half of the ULN range. It is determined that Patient A has reached satisfactory ammonia control.

It is expected that if Patient A adheres to his prescribed diet, his maximal daily ammonia is not expected to exceed approximately 52 μmol/L, i.e., approximately 1.5 times the ULN, with an average likelihood of 75% with 95% confidence. The average ammonia level during the day is expected to remain within normal range with greater than 84% likelihood and 95% confidence. Moreover, Patient A's maximal daily ammonia is highly unlikely to reach 100 μmol/L during the day.

Example 3: Adjusting HPN-100 Dosage Based on Fasting Blood Ammonia Levels in a Patient with UCD Patient B is an 11-year UCD patient receiving 24 pills of BUPHENYL® per day, amino acid supplements, and restricted dietary protein intake. Patient B does not consume BUPHENYL®, supplements, or food for approximately 6 hours prior to a fasting morning blood draw. A venous blood draw is performed, and fasting blood ammonia level is determined to be 40 μmol/L. This fasting blood ammonia level is compared to the ULN for blood ammonia for the laboratory performing the blood draw, which is 35 μmol/L. Based on the correlation of fasting ammonia level to average ammonia level, it is determined that Patient B's fasting blood ammonia level falling between 1 and 1.5 times the ULN represents a 55% chance of having an average ammonia during the day that is greater than the normal range, and as high as a 65% chance that her ammonia will go above 52 μmol/L or 1.5 times ULN during the day.

Based on discussion with the patient and her mother, the physician suspects that Patient B is noncompliant with her medication, and decides to change her to HPN-100. The initial dosage is determined based on the amount of BUPHENYL® Patient B was receiving, and it is determined that Patient B needs to take 10.5 mL of HPN-100 per day. Patient B is treated with 3.5 mL of HPN-100 3 times a day for at least 7 days, and returns for additional blood draws. Her fasting blood ammonia level at this time is 17 µmol/L, which is below the ULN and falls into the range of 0 to 0.5 times normal. It is determined that Patient B has reached satisfactory ammonia control.

It is expected that if Patient B adheres to her prescribed diet, her maximal daily ammonia will not go above approximately 50 µmol/L, which is less than 1.5 times the ULN. Her average ammonia level during the day is expected with greater than 84% average likelihood to remain within normal range. Moreover, there is only a small chance (7%) that Patient B's maximal daily ammonia will exceed 100 µmol/L during the day.

Example 4: Selecting and Adjusting Sodium Benzoate Dosage Based on Fasting Blood Ammonia Levels in a Patient with UCD Patient C is an adult UCD patient who is allergic to PBA and is therefore being managed with amino acid supplements and dietary protein restriction only. Patient C complains of chronic headache and frequent nausea. Patient C consumes neither his supplements nor food for approximately 8 hours prior to a fasting morning blood draw. A venous blood draw is performed, and fasting blood ammonia level is determined to be 77 µmol/L. This fasting blood ammonia level is compared to the ULN for blood ammonia for the laboratory performing the blood draw, which is 35 µmol/L. Based on the correlation of fasting ammonia level to average ammonia level, it is determined that Patient C's fasting blood ammonia level of approximately 2 times the ULN represents a high likelihood of ammonia levels going over 100 µmol/L during the day. Thus, the ratio of fasting blood ammonia level to ULN for blood ammonia indicates that Patient C will benefit from treatment with a nitrogen scavenging drug.

The physician decides to treat Patient C with 15 g of sodium benzoate per day since the patient is allergic to PBA. Patient C is treated with 15 g/day of sodium benzoate for at least 7 days, and returns for additional blood draws. Fasting blood ammonia level at this time is 35 µmol/L, which is equal to the ULN. Patient C's dosage of sodium benzoate is increased by approximately 30% to 18 grams per day. After at least 7 days of treatment, Patient C's fasting ammonia level is 15 µmol/L, which is less than half of the ULN. It is determined that Patient C has reached satisfactory ammonia control.

It is expected that if Patient C adheres to his prescribed diet and medication, his maximal daily ammonia will not exceed approximately 52 µmol/L, which is approximately 1.5 times the ULN. His average ammonia level during the day is expected with greater than 80% likelihood to remain within normal range. Moreover, Patient C's maximal daily ammonia is highly unlikely to reach 100 µmol/L during the day.

Example 5: Evaluation of the Effect of Ammonia Control on Neurocognitive Outcome It has been shown that UCD patients are likely to suffer from diminished intelligence and impaired neurocognitive functions (Kirvitsky 2009). These neuropsychological impairments have been attributed to repeated episodes of acute hyperammonemia interspersed on chronically elevated ammonia. Abnormalities in neuropsychological function and/or brain imaging have been detected even in UCD patients with mild disorders who exhibit normal IQ and/or appear clinical normal (Gropman 2008a; Gropman 2008b). Therefore, it was hypothesized that maintaining average daily ammonia within normal limits and thereby reducing the long term ammonia burden could result in improved cognition.

The relationship between reducing ammonia burden by maintaining fasting ammonia at or close to half ULN and neuropsychological outcomes in pediatric UCD patients was explored in clinical trials. Eleven pediatric patients ages 6-17 were enrolled in short term switch over comparison of NaPBA and HPN-100 in controlling ammonia. These patients underwent 24-hr serial sample collection in a confined setting where the last sample at 24 hr was considered fasting and under supervision of the study personnel. At the end of treatment with HPN-100 the average fasting ammonia at 24-hr time point was 15.5 µmol/L or less than half ULN, indicating good clinical control. These 11 patients along with another 15 pediatric patients were enrolled in two long term studies and received HPN-100 for 12 months, during which monthly fasting ammonia were collected. At the time of enrollment and at the end of the study, all patients underwent assessment for neuropsychological outcomes including the following: BRIEF (Behavior Rating Inventory of Executive Function) to assess day-to-day executive functioning, CBCL (Child Behavior Checklist) to evaluate internalizing (e.g., mood/anxiety) and externalizing behaviors, and WASI (Wechsler Abbreviated Scale of Intelligence) to estimate of intellectual ability.

During the 12 month treatment with HPN-100, pediatric UCD patients experienced fewer episodes of acute hyperammonemia than in the 12 months preceding enrollment (5 episodes during the study versus 9 before enrollment), with peak ammonia dropping from a mean of 233 µmol/L before enrollment to 166 µmol/L during the study. Fasting ammonia remained controlled and monthly averages were at or close to half ULN, ranging from 17 to 22 mol/L. Although patients had been instructed to remain fasting before monthly study visits, some ammonia samples were taken in a non-fasted state, resulting in average monthly ammonia of slightly above half ULN.

In pediatric patients, WASI and CBCL scores were stable in comparison to baseline. The majority of the BRIEF subscales at baseline were at or close to 65, consistent with borderline and/or clinically significant dysfunction. Among 22 pediatric subjects who completed the neuropsychological testing at 12 months, all BRIEF domains were improved (lower T scores) with means (SD) at end of study compared to baseline for Behavioral Regulation Index 53.7 (9.79) vs. 60.4 (14.03) ($p<0.05$); Metacognition Index 57.5 (9.84) vs. 67.5 (13.72) ($p<0.001$), and Global Executive Scale 56.5 (9.71) vs. 66.2 (14.02) ($p<0.001$).

The significant improvement in executive functions in this group of pediatric UCD patients indicates the importance of long term ammonia control and achieving target levels of fasting ammonia.

Example 6: Correlation of Elevated PAA Levels to Neurological AEs in UCD and Healthy Subjects Elevated plasma levels of PAA may cause symptoms that mimic those associated with hyperammonemia, including headache, nausea, somnolence, etc. Since such symptoms are common and nonspecific, an ammonia level below half the upper limit of normal in a subject with a nitrogen retention disorder who exhibits such symptoms and is receiving a PAA prodrug would prompt a physician to check plasma PAA levels.

The relationship between elevated PAA levels and neurological AEs was evaluated in three populations: (1) 130 healthy adults dosed with 4 to 12 mL TID of GPB in a thorough QTc study, (2) 54 adult and 11 pediatric UCD patients (ages 6-17) enrolled in one of 3 protocols involving short term (2-4 week) switchover comparisons of NaPBA vs. GPB, and (3) 77 patients enrolled in two nearly identical 12-month GPB treatment protocols. In populations 1 and 2, maximal PAA (i.e., Cmax) levels were analyzed in relation to neurological AEs as defined by MEDDRA using an Exact non-parametric Mann-Whitney test and Generalized Estimating Equations (GEE) with a logit link function and effects for dose and PAA level. The relationship between PAA levels and the occurrence of the AEs reported by Thiebault was also explored in population 3.

No statistically significant relationship was observed between neurological AEs and PAA levels for either GPB or NaPBA. The odds ratio of a neurological AE occurring for each 20 µg/mL increase in PAA levels for the two drugs combined was 0.95, very close to 1. Thus, among UCD patients dosed with HPN-100 or NaPBA over the ranges used in these studies, increasing levels of PAA (ranging up to 244 µg/mL) were not associated with an increase in neurological AEs. Similarly, in population 3, PAA levels did not increase over time and exhibited no apparent relationship to neurological AEs, which also did not increase in frequency over time. The pediatric patient with the highest PAA level (410 µg/mL) did not report neurological AEs close to the timing of the blood draw.

Unlike UCD subjects, healthy adult volunteers who reported a nervous system AE had statistically significantly higher PAA $C_{max}$ levels than those who did not. While this analysis in healthy adults is compromised by the fact that PAA levels were not always available at the time of occurrence of the AEs, as well as by the small sample size in the higher dose groups, the odds ratio of 1.75 (p=0.006) suggests that increasing levels of PAA are associated with increased probability of experiencing a nervous system AE among healthy adults. AEs reported by healthy adults generally began within 36 hours of dosing and, among those adults who remained on study, most resolved with continued dosing.

A significant relationship between PAA levels and occurrence of neurological AEs, which generally resolved with continued dosing, was detected in healthy volunteers. Unlike in healthy adults, PAA $C_{max}$ did not correlate with nervous system AEs in UCD patients over a similar range of doses and PAA levels. These findings may reflect metabolic differences among the populations (e.g., UCD patients exhibit high glutamine levels compared with healthy humans) and/or metabolic adaptation with continued dosing.

Population PK model building was performed on 65 UCD patients who participated in the short-term switchover Hyperion studies using NONMEM (version 7.2) based on 2981 ([PBA], [PAA], [PAGN], and urine PAGN [UPAGN])) data points from 53 adult and 11 pediatric UCD patients (ages 6-17) who participated in 3 switchover studies of NaPBA and GPB. The median GPB dose, expressed as grams of PBA per m2, was 8.85 and 7.01 for pediatric and adult subjects, respectively. Diagnostic plots and statistical comparisons were used to select among candidate models, and covariates were assessed by graphical analyses and covariate modeling. Using the final popPK model and parameter estimates, Monte Carlo simulations were performed in ~1000 virtual patients for a range of NaPBA and GPB doses to predict systemic metabolite exposure and UPAGN output.

The final model that best fit the data was characterized by (a) partial conversion of PBA to PAGN prior to reaching the systemic circulation, (b) saturable conversion of PAA to PAGN (Km ~161 ug/ml), and (c) ~60% slower PBA absorption when delivered as GPB vs. NaPBA. Body surface area (BSA) was a significant covariate such that metabolite clearance was proportionally related to BSA. Fractional presystemic metabolism of PBA was higher for adults than for pediatric patients receiving GPB (43% vs. 14%), whereas the reverse was true for NaPBA (23% vs. 43%). Predicted median PAA exposure based on simulated GPB dosing at the PBA equivalent of 13 g/m2 of NaPBA was ~13%-22% lower in adults than NaPBA (Cmax=82 vs. 106 µg/mL; $AUC_{0-24}$=649 vs. 829 µg·h/m) and ~13% higher in pediatric subjects ages 6-17 than NaPBA (Cmax=154 vs. 138 µg/mL; $AUC_{0-24}$=1286 vs. 1154 µg·h/ml); predicted upper 95th percentile PAA exposure was below 500 µg/mL and 25%-40% lower for adult subjects on GPB versus NaPBA and similar for pediatric subjects. Simulated dosing at the PBA equivalent of ~5 g/m$^2$ of NaPBA yielded similar and less variable PAA exposure for both drugs and for pediatric and adult patients. Recovery of PBA as UPAGN was very similar whether delivered orally as GPB or NaPBA.

These findings based on PopPK modeling and dosing simulations suggest that while most patients treated with PAA prodrugs including NaPBA or HPN-100 will have PAA levels below those reportedly associated with toxicity and while no relationship between PAA levels and neurological AEs was found on a population basis, individual patients exhibiting symptoms such as headache or nausea might be suffering from either hyperammonemia or high PAA levels and that a fasting ammonia level equal to or below half the upper limit of normal would prompt the physician to check plasma PAA levels.

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Brusilow Science 207:659 (1980)
2. Brusilow Pediatr Res 29:147 (1991)
3. Diaz Mol Genet Metab 102:276 (2011)
4. Gropman Mol Genet Metab 94:52 (2008a)
5. Gropman Mol Genet Metab 95:21 (2008b)
6. Lee Mol Genet Metab 100:221 (2010)
7. Liang Biometrika 73:13 (1986)
8. Lichter-Konecki Mol Genet Metab 103:323 (2011)
9. McGuire Hepatology 51:2077 (2010)
10. Thiebault Cancer Res 54:1690 (1994)
11. Thiebault Cancer 75:2932 (1995)

What is claimed is:
1. A method of treating a subject with a urea cycle disorder (UCD) who has a fasting plasma ammonia level less than the upper limit of normal and who is not experiencing a hyperammonemic crisis and wherein the UCD is not related to N-acetylglutamate synthase, the method comprising:

a) orally administering an initial dosage of glyceryl tri[4-phenylbutyrate];

b) after a time period sufficient for the glyceryl tri-[4-phenylbutyrate] to reach steady state, measuring a single fasting plasma ammonia level for the subject and not serial blood draws;

c) comparing the fasting plasma ammonia level to the upper limit of normal, wherein the upper limit of normal is relative to the reference range of normal values at the laboratory in which the ammonia was measured; and d) orally administering an adjusted dosage of glyceryl tri-[4-phenylbutyrate], wherein the adjusted dosage is greater than the initial dosage if the fasting plasma ammonia level is greater than half the upper limit of normal for plasma ammonia level, wherein a subject with a fasting ammonia in the range 0-0.5 ULN has a greater than 80% likelihood of having an average daily ammonia level within a normal range.

2. The method of claim 1, wherein the time period sufficient for the glyceryl tri-[4-phenylbutyrate] to reach steady state is 48 hours.

3. The method of claim 1, wherein the time period sufficient for the glyceryl tri-[4-phenylbutyrate] to reach steady state is 48 to 72 hours.

4. The method of claim 1, wherein the time period sufficient for the glyceryl tri-[4-phenylbutyrate] to reach steady state is 72 hours to 1 week.

5. The method of claim 1, wherein the time period sufficient for the glyceryl tri-[4-phenylbutyrate] to reach steady state is 1 week to 2 weeks.

6. The method of claim 1, wherein the time period sufficient for the glyceryl tri-[4-phenylbutyrate] to reach steady state is greater than 2 weeks.

7. The method of claim 1, further comprising repeating steps (b) to (d) until the subject exhibits a fasting plasma ammonia level at or below half the upper limit of normal for plasma ammonia level.

8. The method of claim 1, wherein the upper limit of normal for plasma ammonia level is 35 µmol/L.

9. The method of claim 1, wherein the fasting period for obtaining a fasting blood ammonia level is overnight.

* * * * *